(12) United States Patent
Dieterle et al.

(10) Patent No.: US 8,232,425 B2
(45) Date of Patent: Jul. 31, 2012

(54) PROCESS FOR HETEROGENEOUSLY CATALYZED PARTIAL GAS PHASE OXIDATION OF PROPYLENE TO ACRYLIC ACID

(75) Inventors: Martin Dieterle, Mannheim (DE); Joerg Heilek, Bammental (DE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 788 days.

(21) Appl. No.: 11/564,530

(22) Filed: Nov. 29, 2006

(65) Prior Publication Data

US 2007/0149807 A1  Jun. 28, 2007

Related U.S. Application Data

(60) Provisional application No. 60/752,362, filed on Dec. 22, 2005.

(30) Foreign Application Priority Data

Dec. 22, 2005 (DE) .......................... 10 2005 062 010

(51) Int. Cl.
*C07C 51/42* (2006.01)
(52) U.S. Cl. ........ 562/600; 562/512; 562/532; 562/598; 562/599
(58) Field of Classification Search .................. 562/532, 562/600
See application file for complete search history.

(56) References Cited

U.S. PATENT DOCUMENTS

| | | | |
|---|---|---|---|
| 4,413,147 A | 11/1983 | Khoobiar | |
| 4,532,365 A | 7/1985 | Khoobiar | |
| 4,535,188 A | 8/1985 | Khoobiar | |
| RE32,082 E | 2/1986 | Khoobiar | |
| 6,410,785 B1 | 6/2002 | Zehner et al. | |
| 6,448,439 B1 * | 9/2002 | Eck et al. ....................... | 562/600 |
| 6,781,017 B2 * | 8/2004 | Machhammer et al. ...... | 568/470 |
| 6,888,024 B2 | 5/2005 | Dieterle et al. | |
| 7,238,827 B2 | 7/2007 | Hechler et al. | |
| 2004/0015013 A1 * | 1/2004 | Hammon et al. ............. | 562/532 |
| 2004/0116741 A1 | 6/2004 | Nordhoff et al. | |
| 2004/0138501 A1 | 7/2004 | Thiel et al. | |
| 2004/0181083 A1 | 9/2004 | Proll et al. | |
| 2005/0222459 A1 | 10/2005 | Nordhoff et al. | |
| 2006/0004227 A1 | 1/2006 | Dieterle et al. | |
| 2006/0004229 A1 | 1/2006 | Dieterle et al. | |
| 2006/0258529 A1 | 11/2006 | Diefenbacher et al. | |

FOREIGN PATENT DOCUMENTS

| | | |
|---|---|---|
| DE | 33 13 573 A1 | 10/1983 |
| DE | 3521 458 A1 | 12/1985 |
| DE | 199 02 562 A1 | 7/2000 |
| DE | 101 31 297 A1 | 1/2003 |
| DE | 102 45 585 A1 | 4/2004 |
| DE | 103 13 208 A1 | 10/2004 |
| DE | 10 2005 009 885 A1 | 9/2006 |
| DE | 10 2005 010 111 A1 | 9/2006 |
| DE | 10 2005 022 798 A1 | 11/2006 |
| EP | 253409 A2 * | 1/1988 |
| GB | 2 160 543 A | 12/1985 |
| WO | WO 01/96270 A2 | 12/2001 |
| WO | WO 02/055469 A1 | 7/2002 |
| WO | WO 03/011804 A2 | 2/2003 |
| WO | WO 03/078378 A1 | 9/2003 |
| WO | WO 2004/063138 A1 | 7/2004 |
| WO | WO 2006/002703 A1 | 1/2006 |

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

A process for heterogeneously catalyzed partial gas phase oxidation of propylene to acrylic acid, in which the starting reaction gas mixture comprises cyclopropane as an impurity and the acrylic acid, after conversion from the product gas mixture into the condensed phase, is removed with the aid of a crystallative removal.

32 Claims, No Drawings

PROCESS FOR HETEROGENEOUSLY CATALYZED PARTIAL GAS PHASE OXIDATION OF PROPYLENE TO ACRYLIC ACID

BACKGROUND OF THE INVENTION

1. Field of the Invention

The present invention relates to a process for heterogeneously catalyzed partial gas phase oxidation of propylene to acrylic acid, in which, in a first reaction zone, a starting reaction gas mixture 1 which comprises propylene, molecular oxygen and at least one inert diluent gas and comprises the molecular oxygen and the propylene in a molar $O_2:C_3H_6$ ratio of $\geq 1$, in a first reaction stage at elevated temperature, is first conducted through at least one first catalyst bed whose catalysts have at least one multimetal oxide comprising Mo, Fe and Bi as the active composition, such that the propylene conversion in single pass through the catalyst bed is $\geq 90$ mol % and the accompanying selectivity $S^{AC}$ of acrolein formation and of acrylic acid by-product formation together is $\geq 80$ mol %, the temperature of the product gas mixture 1 leaving the first reaction stage is, if appropriate, reduced by direct cooling or by indirect cooling or by direct and indirect cooling, and, if appropriate, secondary gas in the form of molecular oxygen or inert gas or molecular oxygen and inert gas is added to product gas mixture 1, and then product gas mixture 1, as a starting reaction gas mixture 2 which comprises acrolein, molecular oxygen and at least one inert diluent gas and comprises the molecular oxygen and the acrolein in a molar $O_2:C_3H_4O$ ratio of $\geq 0.5$, in a second reaction stage at elevated temperature, is conducted through at least one second catalyst bed whose catalysts have at least one multimetal oxide comprising Mo and V as the active composition, such that the acrolein conversion in single pass through the catalyst bed is $\geq 90$ mol % and the selectivity $S^{AA}$ of acrylic acid formation assessed over both reaction stages, based on propylene converted, is $\geq 70$ mol %, then the acrylic acid present in the product gas mixture 2 formed in the second reaction stage, in a first separation zone, is converted therefrom to the condensed phase and then, in a second separation zone, the acrylic acid is removed from the condensed phase by use of at least one thermal separation process.

2. Description of the Background

As a partial oxidation product of propylene, acrylic acid is a significant monomer which finds use, as such or in the form of its alkyl esters, for obtaining polymers suitable, for example, as adhesives or water-superabsorbing polymers (cf. for example, WO 02/055469 and WO 03/078378).

The preparation of acrylic acid by a process described at the outset of this document is known (cf., for example, DE-A 102 45 585, WO 03/011804, DE-A 101 31 297, WO 01/96270).

The propylene required as a starting substance for this procedure is adding to starting reaction gas mixture 1 typically as crude propylene. In contrast to chemically pure propylene, crude propylene also comprises constituents chemically different from propylene (impurities) which, based on the crude propylene, may be up to 10% by volume and more. For example, the crude propylene may also be the product gas mixture of a heterogeneously catalyzed partial propane dehydrogenation (cf. DE-A 102 45 585 and DE-A 10 2005 022 798). In principle, it is possible to remove all impurities present in crude propylene from the propylene present therein (cf., for example, DE-A 35 21 458 and DE-A 102 45 585). However, this is not necessary when the impurities behave inertly in the heterogeneously catalyzed partial oxidation of propylene to acrylic acid. When they have the latter property, the impurities act simply as inert diluent gases in starting reaction gas mixture 1 (cf. WO 01/96270 and DE-A 33 13 573). In this document, this refers quite generally to those gases which, in the course of the partial oxidation, each alone, remain chemically unchanged to an extent of at least 95 mol %, preferably to an extent of at least 97 mol % and most preferably to an extent of 99 mol % or more. In the course of the conversion of the acrylic acid from product gas mixture 2 into the condensed phase, these inert gases typically remain as residual gas in the gas phase and can thus be removed from the target product in a comparatively simple manner after the partial oxidation than would be the case in a removal of propylene prior to the partial oxidation. In relation to the partial oxidation of propylene to acrylic acid, the propanes have hitherto been considered to be such inert diluent gases in the technical literature. The considerations in this connection even go to the extent of replacing propylene as a raw material for preparing acrylic acid by propane as such a raw material. In this case, propane is dehydrogenated partially to propylene in a first step and the propylene formed in the first step is subsequently partially oxidized to acrylic acid under heterogeneous catalysis in the presence of the unconverted propane (cf. WO 01/96270). Normally, propane in such a resulting starting reaction gas mixture 1 even formed the main constituent. Recycling of the residual gas which comprises unconverted propane and remains in the condensation of the target product out of the product gas mixture into the dehydrogenation and/or partial oxidation allows the propane in this way finally to be converted fully to acrylic acid (cf., for example, DE-A 02 45 585, DE-A 10 2005 009 885, DE-A 10 2005 010 111). Although a vanishingly small amount of the propane (its order of magnitude based on its use amount is 0.01% by weight) can be converted to propionic acid (which is an undesired companion to acrylic acid merely owing to its unpleasant odor even in the smallest amounts and owing to its incapability of polymerizing in a free-radical manner), such a small by-product conversion can be counteracted, for example, by diluting the starting reaction gas mixture 1 comprising propane additionally with an inert diluent gas other than propane (e.g. $N_2$, $H_2O$, $CO_2$, noble gas, mixtures of these gases, etc.) (cf., for example, WO 01/96270).

However, the above-described considerations are no longer valid when the propylene contamination does not behave inertly in a heterogeneously catalyzed partial oxidation thereof to acrylic acid, but is instead converted in significant fractions to a by-product of acrylic acid formation. This is attributable to the fact that the by-product formed normally cannot be discharged as a target product impurity with the target product. Instead, in many cases, even small target product contaminations, with a view to the desired target product use, have a troublesome effect (for example, in the case of use of the acrylic acid to prepare polyacrylic acids and/or their fully and/or partly neutralized alkali metal salts, which are used predominantly as water-superabsorbing materials in the hygiene sector; or in the case of use of the acrylic acid for preparing its alkyl esters and the use of the latter for preparing polymers suitable as adhesives) and then have to be removed in a second separation zone using at least one thermal separation process from the phase which comprises the target product in condensed form and is formed in the first separation zone (or vice versa). Such a removal can be comparatively costly and inconvenient. In such cases, attempts will appropriately be made to remove the appropriate propylene impurity prior to the partial oxidation.

In many cases, a parallel procedure is also used. In other words, a portion of the propylene impurity is removed prior to the propylene partial oxidation, and the remaining portion is, after the propylene partial oxidation has been carried out, removed from the acrylic acid as an acrylic acid by-product in separation zone 2 by means of at least one thermal separation process (or vice versa).

Thermal separation processes should be understood to mean those processes in which at least two substance phases different from one another (for example liquid/liquid; gaseous/liquid; solid/liquid; gaseous/solid, etc.) are generated and contacted with one another. Owing to the inequilibrium existing between the phases, there is heat and mass transfer between them, which ultimately causes the desired separation (removal). The term thermal separation processes reflects that either the withdrawal or the supply of heat is required to generate the formation of the substance phases and/or that the withdrawal or the supply of thermal energy promotes or maintains the mass transfer.

Thermal separation processes in the context of the present invention are therefore distillations, rectifications, crystallizations, extractions, azeotropic distillations, azeotropic rectifications, stripping, desorption, etc. (cf. also WO 04/063138).

Crystallizative thermal separation processes are considered to be particularly capital-intensive and attempts are therefore generally made to avoid them.

SUMMARY OF THE INVENTION

Surprisingly, it has now been found in the course of in-house studies that cyclopropane, a common companion of propylene in crude propylene, does not form an inert gas in the context of a heterogeneously catalyzed partial oxidation of propylene to acrylic acid as described at the outset. In the course of heating to from 100 to 200° C. in the presence of catalysts (e.g. Pt), cyclopropane isomerizes to propylene (for example Lehrbuch der Organischen Chemie [Textbook of organic chemistry], Beyer•Walter, Hirzel Verlag Stuttgart, page 390, 1991). In the course of a heterogeneously catalyzed partial oxidation of propylene to acrylic acid as described at the outset, however, it behaves quite differently to propylene and does not, like propylene, react virtually exclusively to give acrylic acid, but instead, in an entirely unexpected manner, to a high and surprisingly considerable degree, to give propionic acid. It was therefore an object of the present invention to work with this surprising chance finding in the context of a preparation of, for example, acrylic acid very low in propionic acid via the route of a two-stage heterogeneously catalyzed partial oxidation of propylene to acrylic acid. This is also against the background that the aforementioned isomerization to propylene might be a suitable route for eliminating the cyclopropane prior to the partial oxidation. In principle, propylene and cyclopropane can also be separated from one another by rectification, given that their boiling points at standard pressure (1 bar) are sufficiently different from one another (propylene b.p.=−47° C.; cyclopropane b.p.=−32.8° C.). The aforementioned question and its answer is of particular interest in particular when at least a portion of the residual gas which remains in separation zone 1 and would comprise incompletely converted cyclopropane in the partial oxidation is recycled at least partly as cycle gas into the partial oxidation as a constituent of starting reaction gas mixture 1, given that such a cycle gas method in continuous operation would be accompanied by accumulation of the cyclopropane in starting reaction gas mixture 1.

As a solution to the object of the invention, it has now been found that it is appropriate, at least up to cyclopropane contents of 3 mol % based on the propylene present in starting reaction gas mixture 1, to leave the cycloalkane in the crude propylene as an impurity and to remove the propionic acid formed therefrom in the partial oxidation from the acrylic acid target product by virtue of the at least one thermal separation process in the second separation zone (in separation zone 2) comprising at least one crystallizative removal of acrylic acid (owing to comparable condensation points (at 1 bar, acrylic acid: 141° C., propionic acid: 141.35° C.), the propionic acid is converted to the condensed phase in separation zone 1 normally together with the acrylic acid (i.e. as a companion to acrylic acid)).

Accordingly, the present application claims a process for heterogeneously catalyzed partial gas phase oxidation of propylene to acrylic acid, in which, in a first reaction zone, a starting reaction gas mixture 1 which comprises propylene, molecular oxygen and at least one inert diluent gas and comprises the molecular oxygen and the propylene in a molar $O_2:C_3H_6$ ratio of $\geq 1$, in a first reaction stage (reaction stage 1), is first conducted through at least one first catalyst bed (catalyst bed 1) whose catalysts have at least one multimetal oxide comprising Mo, Fe and Bi as the active composition, such that the propylene conversion in single pass through the catalyst bed is $\geq 90$ mol % and the accompanying selectivity $S^{AC}$ of acrolein formation and of acrylic acid by-product formation together is $\geq 80$ (preferably $\geq 85$, or $\geq 90$) mol %, the temperature of the product gas mixture 1 leaving the first reaction stage is, if appropriate, reduced by direct cooling or by indirect cooling or by direct and indirect cooling, and, if appropriate, secondary gas in the form of molecular oxygen or inert gas or molecular oxygen and inert gas is added to product gas mixture 1, and then product gas mixture 1, as a starting reaction gas mixture 2 which comprises acrolein, molecular oxygen and at least one inert diluent gas and comprises the molecular oxygen and the acrolein in a molar $O_2:C_3H_4O$ ratio of $\geq 0.5$, in a second reaction stage (reaction stage 2) at elevated temperature, is conducted through at least one second catalyst bed (catalyst bed 2) whose catalysts have at least one multimetal oxide comprising Mo and V as the active composition, such that the acrolein conversion in single pass through the catalyst bed is $\geq 90$ mol % and the selectivity $S^{AA}$ of acrylic acid formation assessed over both reaction stages, based on propylene converted, is $\geq 70$ (preferably $\geq 75$, or $\geq 80$) mol %, then the acrylic acid present in the product gas mixture 2 formed in the second reaction stage, in a first separation zone (separation zone 1), is converted therefrom to the condensed phase and then, in a second separation zone (separation zone 2), the acrylic acid is removed from the condensed phase by use of at least one thermal separation process,
wherein
starting reaction gas mixture 1, based on the molar amount of propylene present therein, comprises from >0 up to 3 mol % of cyclopropane and the at least one thermal separation process in the second separation zone comprises at least one crystallizative removal of acrylic acid (from a condensed liquid phase).

DESCRIPTION OF THE INVENTION

Crystallizative removal of acrylic acid is understood to mean that the acrylic acid accumulates in the crystals formed and the secondary components in the mother liquor remaining.

Thus, the process according to the invention is also especially suitable when starting reaction gas mixture 1, based on the molar amount of propylene present therein, comprises from 10 molppb to 3 mol %, or from 50 molppb to 2 mol %, or from 100 molppb to 1 mol %, or from 1 molppm to 8000 molppm, or from 10 molppm to 5000 molppm, or from 100 molppm to 3000 molppm, or from 200 molppm to 2500 molppm, or from 300 molppm to 2000 molppm, or from 400 molppm, or 500 molppm to 1500 molppm, or from 750 to 1250 molppm of cyclopropane.

Useful processes for converting acrylic acid present in product gas mixture 2 to the condensed phase (the gas phase which generally remains is referred to as residual gas in this document) in separation zone 1 in the process according to the invention are in principle all processes known in this regard in the prior art. They essentially feature the conversion of the target product (the acrylic acid) by absorptive and/or condensative (cooling) measures from the gaseous to the condensed phase.

Useful absorbents are, for example, water, aqueous solution and/or organic (especially hydrophobic) solvents (cf. DE-A 103 36 386, DE-A 196 31 645, DE-A 195 01 325, EP-A 982 289, DE-A 198 38 845, WO 02/076917, EP-A 695 736, EP-A 778 225, EP-A 1 041 062, EP-A 982 287, EP-A 982 288, U.S. 2004/0242826, EP-A 792 867, EP-A 784 046, EP-A 695 736 and the literature cited in this regard in these documents).

The acrylic acid present in product gas mixture 2 may also be converted to the condensed phase by full or else by fractional condensation (for example WO 04/035514, DE-A 199 24 532, DE-A 198 14 387, DE-A 197 40 253, DE-A 197 40 252, DE-A 196 27 847 and the literature cited in this regard in these documents).

Both the absorptive and the condensative conversion of acrylic acid to the liquid phase are typically undertaken in separation columns comprising separating internals (for enlarging the mass transfer surface area). Useful separating internals include all known internals. In other words, it is possible to use either trays such as bubble-cap trays, dual-flow trays or valve trays, random packings, for example Raschig rings, or structured packings, for example Sulzer packings, as separating internals. Product gas mixture 2 is generally conducted into the separation column ascending from the bottom upward. In the context of an absorptive condensation, the absorbent is normally moved (conducted) from the top downward in the separation column. The liquid absorbate running downward forms the condensed phase comprising the acrylic acid (and secondary components having a higher and similar boiling point, such as propionic acid). In the fractional condensation, the relatively high-boiling constituents of product gas mixture 2 are condensed ascending into it. The condensate comprising enriched acrylic acid is generally conducted out of the condensation column via side draw removal. It will be appreciated that absorption and condensation may also be employed superimposed on one another. This is, for example, always the case when heat is withdrawn additionally from the system in the absorption process by direct and/or indirect cooling.

Preference is given to conducting product gas mixture 2 into the separation column with a temperature reduced by indirect cooling, or by direct cooling or by direct and indirect cooling. The indirect cooling is undertaken in indirect heat exchangers in a manner known per se, while direct cooling is typically effected by spraying absorbent precooled in a quench apparatus or precooled bottoms liquid from the separation column into product gas mixture 2. A common feature of the above-described absorptive and/or condensative processes (separation processes) is that, at the top of the particular separation column comprising separating internals, into whose lower section product gas mixture 2, appropriately after preceding direct and/or indirect cooling thereof as described, is typically conducted, a residual gas stream normally remains which comprises mainly those constituents of product gas mixture 2 whose boiling point at standard pressure (1 bar) is $\leq -20°$ C. (i.e. the constituents which are difficult to condense or else more volatile).

These include, for example, molecular nitrogen used additionally in the partial oxidation as an inert diluent gas, excess molecular oxygen remaining relative to the reaction stoichiometry in the partial oxidation, carbon oxides formed as a by-product or used additionally as inert diluent gases in starting reaction gas mixture 1, but also propylene unconverted in the partial oxidation and unconverted cyclopropane. In general, the remaining residual gas will, for example, also still comprise fractions of steam. Appropriately in accordance with the invention, at least a portion of such a residual gas will be recycled into the partial oxidation as a constituent of starting reaction gas mixture 1. Appropriately from an application point of view, such a cycle gas method can also be effected via a heterogeneously catalyzed partial dehydrogenation and/or oxydehydrogenation of propane upstream of the inventive partial oxidation as the propylene source. Frequently, in the process according to the invention, at least 10% by volume, or at least 20% by volume, or at least 30% by volume, but usually not more than 80% by volume, or not more than 60% by volume, or not more than 40% by volume of the residual gas will be recycled into the partial oxidation (but generally substantially fully, the total amount of unconverted propane and/or propene present therein and of unconverted cyclopropane with them). A portion of this recycling can also be effected into the second reaction stage, i.e. as a constituent of starting reaction gas mixture 2.

A cycle gas method carried out as described can firstly function as the inert gas source and generally increases the desired target product yield (based on amount of raw material used). It is also possible in principle to feed the entirety and/or a portion of the residual gas to incineration (for example for energy generation), as described, for example, in EP-A 925 272.

Absorptive and/or condensative removals of acrylic acid from product gas mixtures 2 are also described in the documents EP-A 1 388 533, EP-A 1 388 532, DE-A 102 35 847, WO 98/01415, EP-A 1 015 411, EP-A 1 015 410, WO 99/50219, WO 00/53560, WO 02/09839, DE-A 102 35 847, WO 03/041833, DE-A 102 23 058, DE-A 102 43 625, DE-A 103 36 386, EP-A 854 129, U.S. Pat. No. 4,317,926, DE-A 198 37 520, DE-A 196 06 877, DE-A 195 01 325, DE-A 102 47 240, DE-A 197 40 253, EP-A 695 736, EP-A 1 041 062, EP-A 117 146, DE-A 43 08 087, DE-A 43 35 172, DE-A 44 36 243, DE-A 103 32 758 and DE-A 199 24 533.

An absorptive and/or condensative removal of acrylic acid from product gas mixture 2 can also be carried out as described in DE-A 103 36 386, DE-A 101 15 277, DE-A 196 06 877, EP-A 920 408, EP-A 1 068 174, EP-A 1 066 239, EP-A 1 066 240, WO 00/53560, WO 00/53561, DE-A 100 53 086, WO 01/96271, or as described in DE-A 10 2004 032 129 and its equivalent patents. Favorable removal methods are also the processes described in the documents WO 04/063138, WO 04/35514, DE-A 102 43 625 and DE-A 102 35 847. In principle, the acrylic acid can also be frozen out of product gas mixture 2 in the first separation zone.

The further removal of the acrylic acid from the condensed phase can thus be undertaken in the process according to the invention, depending on the procedure employed in separation zone 1 and depending on the specific process conditions which have been selected for the partial oxidation and thus determine the spectrum of other secondary components (reaction temperature, inert diluent gases selected, catalysts selected, content and molar ratio of the reactants in starting reaction gas mixture 1, etc.), up to the desired degree of purity of the acrylic acid by a wide variety of different combinations of a wide variety of different thermal separation processes. These may be, for example, combinations of extractive, desorptive, rectificative, azeotropically distillative, azeotropically rectificative, distillative and/or stripping processes.

It is essential to the invention merely that the combination of the thermal separation processes employed overall for the further removal of the acrylic acid in separation zone 2 comprises at least one crystallizative removal of acrylic acid. This requirement is caused by a crystallizative removal of acrylic acid being associated with increased propionic acid depletion, whereas such a depletion cannot be achieved with other thermal separation processes. In other words, crystals in which acrylic acid is present in enriched form are separated in the process according to the invention from at least one liquid phase which comprises acrylic acid and is obtained in at least one thermal separation process to be employed in separation zone 2. Normally, the crystals will consist essentially substantially exclusively of acrylic acid.

In principle, at least one crystallizative removal of the acrylic acid in the process according to the invention can be effected from an acrylic acid-containing condensed phase obtained in the conversion of the acrylic acid from product gas mixture 2 into the condensed phase.

For example, the crystallizative removal, following the teaching of DE-A 198 38 845, can be effected directly out of the absorbate comprising absorbed acrylic acid (under some circumstances, this may be subjected beforehand to a stripping and/or desorption in order to remove constituents of substantially higher volatility than acrylic acid from the absorbate before the crystallization; such relatively volatile constituents may, for example, be acetic acid, formic acid and/or lower aldehydes). If appropriate, it is also possible to remove absorbent by distillation before the crystallizative removal, in order thus to increase the content of acrylic acid in the absorbate and in this way to ensure that acrylic acid forms the crystalline phase which separates in the course of cooling (or the crystalline phase which separates and comprises enriched acrylic acid). The aforementioned is true both when the absorbate comprises acrylic acid and an organic solvent having a higher boiling point than acrylic acid (cf., for example, DE-A 198 38 845; possible absorbents are, for example, diphenyl, diphenyl ether, mixtures of the two aforementioned agents, and mixtures of diphenyl, diphenyl ether and dimethyl phthalate) and when the absorbent used was water or an aqueous solution (cf., for example, WO 02/055469 and WO 03/078378). In general, the crystals obtained in the crystallizative removal will additionally be washed as a further separation and purification measure. Useful washing agents are, for example, pure absorbent and/or acrylic acid which has been prepared beforehand and already has the desired purity. In principle, washing can also be effected by sweating. In this case, the crystals are heated and the crystals which have an increased level of impurity and melt at lower temperature become liquid and flow out as wash liquid with the impurities. However, the crystallization can also be effected directly out of the condensate which comprises enriched acrylic acid and is obtained in a fractional condensation (preferably withdrawn by means of side draw removal), as described, for example, by WO 04/035514). In principle, the washing of the separated crystals can also be undertaken in a wash column (this may be a static, a hydraulic or a mechanical wash column, as described, for example, by WO 01/77056).

In principle, the crystallizative treatment of at least one liquid phase P comprising acrylic acid in separation zone 2 to be employed in accordance with the invention is subject to no restriction, including the processes for removing the mother liquor from the crystals (all processes detailed in the prior art mentioned in this document can be employed). In other words, it may be carried out in one or more stages, continuously or batchwise. In particular, it may also be carried out as a fractional (or fractionating) crystallization. Typically, in a fractional crystallization, all stages which generate acrylic acid crystals which are purer than the liquid phase P supplied are known as purification stages and all other stages stripping stages. Appropriately, multistage processes are operated by the countercurrent principle, in which, after the crystallization in each stage, the crystals are removed from the mother liquor and these crystals of the particular stage are fed with the next highest degree of purity, while the crystallization residue of the particular stage is fed with the next lowest degree of purity.

Frequently, the temperature of the liquid phase P in the course of separation of the crystals comprising enriched acrylic acid is between $-25°$ C. and $+14°$ C., in particular between $12°$ C. and $-5°$ C.

For example, the crystallizative removal, required in accordance with the invention, of the acrylic acid from the liquid phase P comprising it may be performed as a layer crystallization (cf. DE-A 26 06 364, EP-A 616 998, EP-A 648 520 and EP-A 776 875). In this crystallization, the crystals are frozen out in the form of continuous, firmly adhering layers. In the simplest case, the deposited crystals are separated from the remaining residual melt (also referred to as mother liquor) by virtue of the residual melt simply flowing off. In principle, a distinction is drawn between "static" and "dynamic" layer crystallization processes. A characteristic feature of dynamic layer crystallization of liquid phases P comprising acrylic acid is forced convection of the liquid phase P. This can be effected by pumped circulation of the liquid phase P through tubes with full flow-through, by introduction of the liquid phase P as a trickle film (for example according to EP-A 616 998) or by introduction of inert gas into a liquid phase P or by pulsation.

In the static processes, the liquid phase P is at rest (for example in tube bundle or plate heat exchangers) and deposits in layers as result of slow temperature reduction on the secondary side. Afterward, the residual melt (mother liquor) is discharged, more highly contaminated fractions are sweated off from the crystal layer by slow temperature increase and the pure product is subsequently melted off (cf. WO 01/77056).

Frequently, the at least one crystallizative removal of the acrylic acid in separation zone will be effected by employing a combination of dynamic and static layer crystallization (cf. EP-A 616 998).

According to the invention, the at least one crystallizative removal of acrylic acid from a liquid phase P (in particular from all liquid phases P detailed by way of example in this document) will, however, preferably be performed according to the teaching of WO 01/77056, WO 02/055469 and WO 03/078378 as a suspension crystallization.

In general, a crystal suspension comprising suspended acrylic acid crystals is obtained by cooling the liquid phase P, the acrylic acid crystals having a lower propionic acid content and the remaining residual melt (mother liquor) a higher propionic acid content (relatively, based on the particular total amount) than the liquid phase P to be purified.

The acrylic acid crystals may grow directly in suspension and/or be deposited as a layer on a cooled wall from which they are subsequently scratched off and resuspended in the residual melt (mother liquor).

All suspension crystals and suspension crystallization processes detailed in WO 01/77056, WO 02/055469, and WO 03/078378 are useful in accordance with the invention. In general, the acrylic acid crystal suspension generated has a solids content of from 20 to 40% by weight.

In addition, all processes specified in the aforementioned WO publications are suitable for the separation of suspension crystals which have formed and mother liquor which remains (for example mechanical separation processes such as centrifugation). Preference is given in accordance with the invention to separating in a wash column (for example a gravimetric, hydraulic or mechanical treatment; cf. WO 01/77056). This is preferably a wash column with forced transport of the deposited acrylic acid crystals. The crystal volume fraction in the crystal bed generally attains values of >0.5. In general, the wash column is operated at values of from 0.6 to 0.75. The wash liquid used is advantageously the melt of acrylic acid crystals purified (removed) beforehand in the wash column. The washing is normally effected in countercurrent. The process according to the invention thus in particular comprises processes which comprise the following process steps:
a) crystallization of acrylic acid out of a liquid phase P;
b) separation of the acrylic acid crystals from the remaining mother liquor (residual melt, liquid residual phase);
c) at least partial melting of the removed acrylic acid crystals and
d) at least partial recycling of the molten acrylic acid crystals to step b) and/or to step a).

Preference is given to effecting step b) by countercurrent washing with acrylic acid crystals which have been removed beforehand, melted and recycled into step b).

Advantageously in accordance with the invention, the liquid phase P comprises water when the inventive crystallizative acrylic acid removal is employed, since formation of acrylic acid crystals in the presence of water, according to the teaching of WO 01/77056 and WO 03/078378, causes a particularly favorable crystal form for the subsequent separation of the crystals from the remaining mother liquor. This is especially true when the crystallization is performed as a suspension crystallization, and even more true when the subsequent mother liquor removal is performed in a wash column, and even more true when the wash liquid used is the melt of acrylic acid crystals which have already been purified in the wash column.

In other words, the crystallizative removal of acrylic acid required in accordance with the invention comprises in particular processes in which the liquid phase P comprising acrylic acid is converted under cold conditions to a crystal suspension consisting of acrylic acid crystals and liquid residual phase (residual melt), the proportion by weight of propionic acid in the acrylic acid crystals being smaller and the proportion by weight of the liquid residual phase (the mother liquor) of propionic acid being greater than the proportion by weight of propionic acid in the liquid phase P, a portion of the remaining mother liquor is removed mechanically if appropriate from the crystal suspension, and the acrylic acid crystals are freed in a wash column of remaining mother liquor, with the proviso that
a) the liquid phase P, based on the acrylic acid comprised therein, comprises from 0.20 to 30% by weight, frequently up to 20% by weight, often up to 10% by weight, of water, and b) the wash liquid used is the melt of acrylic acid crystals purified in the wash column.

In particular, the process according to the invention comprises the aforementioned processes, the liquid phase P comprising $\geq 80\%$ by weight of acrylic acid, or $\geq 90\%$ by weight of acrylic acid or $\geq 95\%$ by weight of acrylic acid.

Moreover, it is advantageous in accordance with the invention when the water content of the liquid phase P in the above-described procedures (or quite generally when the process according to the invention is employed), based on acrylic acid comprised in the liquid phase P, is from 0.2 or 0.4 to 8, or to 10, or to 20, or to 30% by weight, or from 0.6 to 5% by weight, or from 0.60 to 3% by weight.

All of the aforementioned applies in particular when the wash column is a wash column having forced transport of the acrylic acid crystals, in particular when it is a hydraulic or a mechanical wash column according to WO 01/77056 and is operated as detailed therein.

All of the aforementioned is true in particular when the wash column is designed and operated according to the teachings of WO 03/041832 and of WO 03/041833.

According to the invention, the at least one crystallizative removal of acrylic acid need not necessarily be effected directly out of the condensed phase which comprises acrylic acid in condensed form and is obtained in separation zone 1. Instead, the liquid (condensed) phase which comprises acrylic acid and is obtained in separation zone 1 will first be subjected to one thermal separation process or else to a combination of thermal separation processes, in the course of which the acrylic acid-containing liquid phase P to be crystallized is obtained.

In many cases, the acrylic acid-containing liquid phase P to be crystallized in accordance with the invention will thus be the result of use of at least one thermal separation process other than a crystallization (for example distillation, rectification, extraction, destraction, desorption, stripping, azeotropic rectification, adsorption and/or azeotropic distillation) to the acrylic acid-containing condensed (liquid) phase obtained in separation zone 1 and/or to subsequent phases resulting in this application (cf., for example, DE-A 196 06 877). Frequently, the acrylic acid-containing liquid phase P to be treated crystallizatively will be obtained by employing the aforementioned processes repeatedly. For example, the acrylic acid-containing liquid phase P to be crystallized may be crude acrylic acid obtained as in DE-A 103 36 386 from the absorbate, obtained in separation zone 1, of the product gas mixture of the propylene partial oxidation by use of various thermal separation processes other than a crystallization. Such crude acrylic acid to be crystallized in accordance with the invention may also be obtained from an aqueous absorbate obtained in separation zone 1 of the process according to the invention according to the teachings of EP-A 695 736, EP-A 778 255 and EP-A 1 041 062 with additional use of at least one azeotropic distillation.

The propionic acid discharge in the process according to the invention can in principle be disposed exclusively in the at least one crystallizative acrylic acid removal, In this case, the discharge will consist of mother liquor comprising enriched propionic acid.

When the crystallizative removal to be employed in accordance with the invention is performed, for example, by means of a combination of dynamic and static crystallization according to EP-A 616 998, the mother liquor discharge comprising enriched propionic acid will appropriately be disposed in the region of the static crystallization.

Advantageously in accordance with the invention, the distinct separation process of the at least one crystallizative acrylic acid removal in the second separation zone will be coupled in the process according to the invention with at least one indistinct separation process in the first (preferably) and/or second separation zone by recycling the mother liquor remaining in the crystallizative acrylic acid removal at least partly into at least one of the indistinct separation processes.

The basic structure of such a coupled use of indistinct separation processes and the distinct separation process of crystallization is taught, for example, by DE-A 196 06 877, EP-A 792 867 and EP-A 1 484 308, EP-A 1 484 309, EP-A 1 116 709 and in particular EP-A 1 015 410.

An indistinct separation process is defined as a separation process in which the composition of the phase which comprises accumulated target product and is formed when the separation process is employed is dependent markedly upon the composition of the mixture to be separated, while the crystallizative removal required in accordance with the invention is a distinct separation process in that the composition of the acrylic acid crystals which form is substantially independent (ideally there is complete independence) of the composition of the acrylic acid-containing liquid phase P. An absorption and/or fractional condensation used in separation zone 1 to convert acrylic acid from product gas mixture 2 into the condensed phase are indistinct separation processes, as are, for example, an extraction and/or rectification in separation zone 2.

In the case of such a coupling of a distinct separation process in separation zone 2 and of an indistinct separation process in, for example, separation zone 1, the process according to the invention is of increased significance in that, in continuous operation of such a procedure, the propionic acid accumulates in the acrylic acid-containing liquid phase P to be treated crystallizatively in accordance with the invention as a result of the mother liquor recycling, since the mother liquor comprises the propionic acid in enriched form.

Appropriately, a coupling of indistinct and distinct separation to be employed as described in the process according to the invention also has a discharge (this may be the only discharge of the process) for at least one stream comprising enriched propionic acid beyond the mother liquor. For example, the bottoms liquid of a separation column (for example of the absorption or condensation column in separation zone 1) can be used as such a discharge, from which the liquid phase P itself or the stream to be converted to the liquid phase P at a later stage is withdrawn, for example, via side withdrawal and/or top withdrawal.

Alternatively, it is also possible to withdraw a separate propionic acid discharge stream at a point in the separation column (for example that disposed within separation zone 1) at which a propionic acid bulge is present (in addition to the discharge for the liquid phase P), and, from this discharge stream, to enrich the propionic acid in the mother liquor in a second, preferably fractional crystallizative removal (for example combination of dynamic and static crystallization according to EP-A 616 998), and to discharge such mother liquor (preferably from the static crystallization). From the purified crystal fraction can be recycled molten into the separation column and/or introduced into the crystallization of the acrylic acid-containing liquid phase P. In principle, such a propionic acid discharge stream may also be a substream withdrawn from liquid phase P.

It will be appreciated that all process steps performed in separation zones 1, 2 are carried out with inhibition of polymerization. The procedure may be as described in the prior art cited. An outstanding position among the entirety of the available acrylic acid process stabilizers is assumed by dibenzo-1,4-thiazine (PTZ), 4-hydroxy-2,2,6,6-tetra-methylpiperidine 1-oxyl (4-OH-TEMPO) and p-methoxyphenol (MEHQ). They may, for example, each alone or in pairs or as a three-substance mixture, be part of the acrylic acid-containing liquid phase P to be treated crystallizatively in accordance with the invention. Typically, the total amount of polymerization inhibitors present in the liquid phase P, based on acrylic acid present therein, is from 0.001 to 2% by weight.

Overall, the process according to the invention, in spite of the content of cyclopropane in starting reaction gas mixture 1, with the sequence of two-stage partial oxidation of the propylene present in starting reaction gas mixture 1, fractional acrylic acid condensation from product gas mixture 2 of the partial oxidation, suspension crystallization of the acrylic acid condensate withdrawn and removal of the suspension crystals from remaining mother liquor in a wash column using pure crystal melt as a wash liquid, permits, in an efficient manner and using only one crystallization stage, the preparation of acrylic acid suitable for superabsorbents (such acrylic acid may of course also be used for all other uses addressed in WO 02/055469 and WO 03/078378.

Apart from the cyclopropane content of starting reaction gas mixture 1, the process for two-stage heterogeneously catalyzed partial gas phase oxidation of propylene to acrylic acid outlined at the outset of this document is common knowledge (cf., for example, WO 01/36364). The catalyst beds may be fixed beds or fluidized beds. Preference is given in accordance with the invention to the use of fixed catalyst beds in both reaction stages.

In this document, the loading of a (fixed) catalyst bed with starting reaction gas mixture is understood to mean the amount of starting reaction gas mixture in standard liters (=l(STP); the volume in liters that the appropriate amount of starting reaction gas mixture would take up under standard conditions (25° C., 1 bar)) which is conducted through one liter of (fixed) catalyst bed per hour. However, the loading of the (fixed) catalyst bed may also be based only on a constituent of the starting reaction gas mixture. In that case, it is the amount of this constituent in l(STP)/l·h which is conducted through one liter of the (fixed) catalyst bed per hour as a component of the particular starting reaction gas mixture.

The realization of the two-stage heterogeneously catalyzed partial oxidation of propylene to acrylic acid to be carried out in accordance with the invention using an inventive starting reaction gas mixture 1 may specifically be carried out as described in the documents EP-A 700 714 (first reaction stage; as described there, but also in corresponding countercurrent mode of salt bath and starting reaction gas mixture over the tube bundle reactor), EP-A 70 08 93 (second reaction stage; as described there, but also in corresponding countercurrent mode), WO 04/085 369 (especially this document is considered to be an integral part of this document) (as a two-stage process), WO 04/085363, DE-A 103 13 212 (first reaction stage), EP-A 1 159 248 (as a two-stage process), EP-A 1 159 246 (second reaction stage), EP-A 1 159 247 (as a two-stage process), DE-A 199 48 248 (as a two-stage process), DE-A 101 01 695 (two-stage), WO 04/085368 (as a two-stage process), DE-A 10 2004 021 764 (two-stage), WO 04/085362 (first reaction stage), WO 04/085370 (second reaction stage), WO 04/085365 (second reaction stage), WO 04/085367 (two-stage), EP-A 990 636, EP-A 1 007 007 and EP-A 1 106 598.

This is especially true of all working examples contained in these documents. They may be carried out as described in these documents, but with the difference that the starting reaction gas mixture used for the first reaction stage is an inventive starting reaction gas mixture 1. Regarding the remaining parameters, the procedure is as in the working examples of the documents mentioned (especially regarding the fixed catalyst beds and reactant loading of the fixed catalyst beds). When there is supply of molecular secondary oxygen between the two reaction stages in the process according to the invention, this is effected preferably in accordance with the invention in the form of air. However, it can also be effected in the form of pure molecular oxygen or else in the form of another mixture of molecular oxygen and of inert gas. Advantageously in accordance with the invention, secondary oxygen is supplied in such an amount that product gas mixture 2 comprises molecular oxygen, which is yet to be converted. However, the amount of molecular oxygen required for the overall process may also already be added to starting reaction gas mixture 1. In general, the molar ratio of molecular oxygen present in starting reaction gas mixture 1 to propylene present in this mixture is $\geq 1$ and $\leq 3$.

Multimetal oxide catalysts which comprise the elements required in accordance with the invention and are suitable for the particular reaction stage of the two reaction stages have been described many times before and are well known to those skilled in the art. For example, EP-A 253 409 refers on page 5 to corresponding US patents. Suitable catalysts for the particular oxidation stage (reaction stage) are also disclosed by DE-A 4 431 957, DE-A 10 2004 025 445 and DE-A 4 431 949. This is especially true of those of the general formula I in the two aforementioned prior art documents. Catalysts usable for the particular oxidation stage (reaction stage) are disclosed by the documents DE-A 103 25 488, DE-A 103 25 487, DE-A 103 53 954, DE-A 103 44 149, DE-A 103 51 269, DE-A 103 50 812, DE-A 103 50 822.

Possible multimetal oxide compositions comprising Mo, Bi and Fe for the process according to the invention in the first reaction stage are also the multimetal oxide active compositions of the general formula I of DE-A 199 55 176, the multimetal oxide active compositions of the general formula I of DE-A 199 48 523, the multimetal oxide active compositions of the general formulae I, II and III of DE-A 101 01 695, the multimetal oxide active compositions of the general formulae I, II, and III of DE-A 199 48 248 and the multimetal oxide active compositions of the general formulae I, II and III of DE-A 199 55 168, and also the multimetal oxide active compositions specified in EP-A 700 714.

Also suitable for the first reaction stage of the process according to the invention are the multimetal oxide catalysts comprising Mo, Bi and Fe which are disclosed in the documents Research Disclosure No. 497012 of Aug. 29, 2005, DE-A 100 46 957, DE-A 100 63 162, DE-C 3 338 380, DE-A 199 02 562, EP-A 15 565, DE-C 2 380 765, EP-A 8 074 65, EP-A 279 374, DE-A 330 00 44, EP-A 575 897, U.S. Pat. No. 4,438,217, DE-A 19855913, WO 98/24746, DE-A 197 46 210 (those of the general formula II), JP-A 91/294 239, EP-A 293 224 and EP-A 700 714. This applies in particular to the exemplary embodiments in these documents, and among these particular preference is given to those of EP-A 15 565, EP-A 575 897, DE-A 197 46 210 and DE-A 198 55 913. Particular emphasis is given in this context to a catalyst according to Example 1c from EP-A 15 565 and also to a catalyst to be prepared in a corresponding manner but whose active composition has the composition $Mo_{12}Ni_{6.5}Zn_2Fe_2Bi_1P_{0.0065}K_{0.06}O_x \cdot 10SiO_2$. Emphasis is also given to the example having the serial number 3 from DE-A 198 55 913 (stoichiometry: $Mo_{12}Co_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the unsupported multimetal oxide II catalyst according to Example 1 of DE-A 197 46 210. Mention should also be made of the multimetal oxide catalysts of U.S. Pat. No. 4,438, 217. The latter is especially true when these hollow cylinders have a geometry of 5.5 mm×3 mm×35 mm, or 5 mm×2 mm×2 mm, or 5 mm×3 mm×2 mm, or 6 mm×3 mm×3 mm, or 7 mm×3 mm×4 mm (each external diameter×height×internal diameter). Further possible catalyst geometries in this context are extrudates (for example length 7.7 mm and diameter 7 mm; or length 6.4 mm and diameter 5.7 mm).

A multitude of those multimetal oxide active compositions which comprise Mo, Fe and Bi in whose presence the cyclopropane in the first reaction stage is particularly amenable to the undesired side reaction and in the case of whose use the inventive procedure is therefore particularly relevant can be encompassed by the general formula IV

$$Mo_{12}Bi_aFe_bX^1_cX^2_dX^3_eX^4_fO_n \qquad (IV)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in IV other than oxygen.

The aforementioned is true in particular when they are obtained in a manner known per se (see, for example, DE-A 4 023 239) and used in accordance with the invention, for example, shaped in substance to give spheres, rings or cylinders, or else used in the form of coated catalysts, i.e. preshaped inert support bodies coated with the active composition. It will be appreciated that the statement also applies when they are used in powder form as catalysts for the first reaction stage (for example in fluidized bed reactors).

In principle, active compositions of the general formula IV can generally be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions IV are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions IV can be intimately mixed in dry or in wet form. When they are mixed in dry form, the starting compounds are appropriately used as finely divided powders and subjected to calcination after mixing and optional compacting. However, preference is given to intimate mixing in wet form. Typically, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions of the general formula IV may be used for the first reaction stage of the process according to the invention either in powder form or shaped to certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Instead of graphite, it is also possible to use hexagonal boron nitride as an assistant in the shaping, as recommended by DE-A 10 2005 037 678. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. The unsupported catalyst can of course also have spherical geometry, and the spherical diameter can be from 2 to 10 mm.

A hollow cylinder geometry particularly relevant in accordance with the invention is 5 mm×3 mm×2 mm (external diameter×length×internal diameter), especially in the case of unsupported catalysts.

The pulverulent active composition relevant in accordance with the invention, or its pulverulent precursor composition which is yet to be calcined and/or partially calcined, may of course also be shaped by applying to preshaped inert catalyst supports. The coating of the support bodies to produce the coated catalysts is generally performed in a suitable rotatable vessel, as disclosed, for example, by DE-A 2 909 671, EP-A 293 859 or EP-A 714 700. To coat the support bodies, the powder composition to be applied is appropriately moistened and dried again after application, for example by means of hot air. The coating thickness of the powder composition applied to the support body is frequently selected within the range from 10 to 1000 µm, preferably within the range from 50 to 500 µm and more preferably within the range from 150 to 250 µm.

Useful support materials are the customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention is based. The support bodies can have a regular or irregular shape, although preference is given to regularly shaped support bodies having distinct surface roughness, for example spheres or hollow cylinders. It is relevant in accordance with the invention to use substantially nonporous, surface-roughened spherical supports made of steatite whose diameter is from 1 to 10 mm or to 8 mm, preferably from 4 to 5 mm. However, it is also relevant in accordance with the invention to use cylinders whose length is from 2 to 10 mm and whose external diameter is from 4 to 10 mm as support bodies. In the case of rings as support bodies, the wall thickness is also typically from 1 to 4 mm. Annular support bodies to be used in accordance with the invention have a length of from 2 to 6 mm, an external diameter of from 4 to 8 mm and a wall thickness of from 1 to 2 mm. Also relevant as support bodies in accordance with the invention are rings of geometry 7 mm×3 mm×4 mm (external diameter×length×internal diameter). The fineness of the catalytically active oxide compositions to be applied to the surface of the support body is of course adjusted to the desired coating thickness (cf. EP-A 714 700).

Multimetal oxide active compositions relevant in accordance with the invention for the step from propylene to acrolein are also compositions of the general formula V

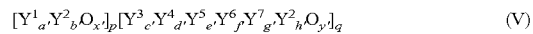  (V)

in which the variables are each defined as follows:
$Y^1$=only bismuth or bismuth and at least one of the elements tellurium, antimony, tin and copper,
$Y^2$=molybdenum, or tungsten, or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'from >0 to 20,
f'=from 0 to 6,
g'=from 0 to 15,
h'=from 8 to 16,
x',y'=numbers which are determined by the valency and frequency of the elements in V other than oxygen and
p,q=numbers whose p/q ratio is from 0.1 to 10,
comprising three-dimensional regions of the chemical composition $Y^1_{a'}Y^2_{b'}O_{x'}$ which are delimited from their local environment owing to their different composition from their local environment, and whose maximum diameter (longest direct line passing through the center of the region and connecting two points on the surface (interface) of the region) is from 1 nm to 100 µm, frequently from 10 nm to 500 nm or from 1 µm to 50 or 25 µm.

Particularly advantageous multimetal oxide compositions V in accordance with the invention are those in which $Y^1$ is only bismuth.

Among these, preference is given in turn to those of the general formula VI

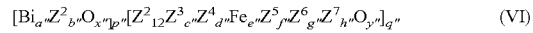  (VI)

in which the variables are each defined as follows:
$Z^2$=molybdenum, or tungsten, or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a''=from 0.1 to 1,
b''=from 0.2 to 2, c''=from 3 to 10,
d''=from 0.02 to 2,
e''=from 0.01 to 5, preferably from 0.1 to 3,
f''=from 0 to 5,
g''=from 0 to 10,
h''=from 0 to 1,
x'',y''=numbers which are determined by the valency and frequency of the elements in VI other than oxygen,
p'',q''=numbers whose p''/q'' ratio is from 0.1 to 5, preferably from 0.5 to 2,
and very particular preference is given to those compositions VI in which $Z^2{}_{b''}$=(tungsten)$_{b''}$ and $Z^2{}_{12}$=(molybdenum)$_{12}$.

It is also significant in accordance with the invention when at least 25 mol % (preferably at least 50 mol % and more preferably at least 100 mol %) of the total proportion of $[Y^1{}_a Y^2{}_b O_x]_p$ ($[Bi_{a''} Z^2{}_{b''} O_{x''}]_{p''}$) of the multimetal oxide compositions V (multimetal oxide compositions VI) suitable in accordance with the invention in the multimetal oxide compositions V (multimetal oxide compositions VI) suitable in accordance with the invention is in the form of three-dimensional regions of the chemical composition $Y^1{}_a Y^2{}_b O_{x'}$, $[Bi_{a''} Z^2{}_{b''} O_{x''}]$ which are delimited from their local environment owing to their different chemical composition from their local environment, and whose maximum diameter is in the range from 1 nm to 100 µm.

With regard to the shaping, the statements made for the multimetal oxide composition IV catalysts apply to multimetal oxide composition V catalysts.

The preparation of multimetal oxide active compositions V is described, for example, in EP-A 575 897 and also in DE-A 198 55 913.

The inert support materials recommended above are also useful, inter alia, as inert materials for the dilution and/or delimitation of the appropriate fixed catalyst beds, or as a preliminary bed which protects them and/or heats the gas mixture. For the second step (the second reaction stage), the heterogeneously catalyzed gas phase partial oxidation of acrolein to acrylic acid, useful active compositions for the catalysts required are, in accordance with the invention, in principle all multimetal oxide compositions comprising Mo and V, for example those of DE-A 100 46 928 and of DE-A 198 15 281.

A multitude thereof which are particularly relevant in accordance with the invention for the undesired reaction of cyclopropane can be encompassed by the general formula VII

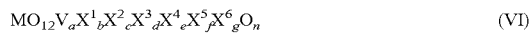  (VI)

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in VII other than oxygen.

Embodiments which are particularly relevant in accordance with the invention among the active multimetal oxides VII are those which are encompassed by the following definitions of the variables of the general formula VII:

$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in VII other than oxygen.

However, multimetal oxides VII which are very particularly relevant in accordance with the invention are those of the general formula VIII

  (VIII)

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in VIII other than oxygen.

The multimetal oxide active compositions (VII) which are relevant in accordance with the invention are obtainable in a manner known per se, for example disclosed in DE-A 43 35 973 or in EP-A 714 700.

Generally, multimetal oxide active compositions relevant in accordance with the invention for the "acrolein→acrylic acid" step, especially those of the general formula VII, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned by themselves). The calcination time can be from a few minutes to a few hours and typically decreases with temperature. Useful sources for the elemental constituents of the multimetal oxide active compositions VII include those compounds which are already oxides and/or those compounds which can be converted to oxides by heating, at least in the presence of oxygen.

The starting compounds for the preparation of multimetal oxide compositions VII can be intimately mixed in dry or in wet form. When they are mixed in dry form, the starting compounds are appropriately used in the form of finely divided powder and subjected to calcining after mixing and, if appropriate, compaction. However, preference is given to intimate mixing in wet form.

This is typically done by mixing the starting compounds with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, especially those of the general formula VII, may be used for the inventive acrolein oxidation either in powder form (for example in fluidized bed reactors) or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of relevant unsupported catalyst geometries are solid cylinders or hollow cylinders having an external diameter and a length of from 2 to 10 mm. In the case of the hollow cylinders, a wall thickness of from 1 to 3 mm is appropriate. The unsupported catalyst may of course also have spherical geometry, in which case the spherical diameter may be from 2 to 10 mm (e.g. 8.2 mm or 5.1 mm).

The pulverulent active composition or its pulverulent precursor composition which is yet to be calcined can of course also be shaped by applying to preshaped inert catalyst supports. The coating of the support bodies to prepare the coated catalysts is generally performed in a suitable rotatable vessel, as disclosed, for example, by DE-A 2 909 671, EP-A 293 859 or by EP-A 714 700.

To coat the support bodies, the powder composition to be applied is appropriately moistened and is dried again after application, for example by means of hot air. The coating thickness of the powder composition applied to the support body is, in a manner relevant in accordance with the invention, frequently selected within the range from 10 to 1000 µm, preferably within the range from 50 to 500 µm and more preferably within the range from 150 to 250 µm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with grit layer. It is suitable to use substantially nonporous, surface-roughened, spherical supports made of steatite, whose diameter is from 1 to 10 mm or to 8 mm, preferably from 4 to 5 mm. In other words, suitable spherical geometries may have diameters of 8.2 mm or 5.1 mm. However, it is also suitable to use cylinders whose length is from 2 to 10 mm and whose external diameter is from 4 to 10 mm as support bodies. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Also relevant are in particular rings of geometry 7 mm×3 mm×4 mm (external diameter×length×internal diameter). The fineness of the catalytically active oxide compositions to be applied to the surface of the support body is of course adapted to the desired coating thickness (cf. EP-A 714 700).

Multimetal oxide active compositions relevant for the inventive "acrolein→acrylic acid" step are also compositions of the general formula IX $$[D]_p[E]_q \quad \text{(IX)}$$

in which the variables are each defined as follows:

$D = Mo_{12}V_{a''}Z^1_{b''}Z^2_{c''}Z^3_{d''}Z^4_{e''}Z^5_{f''}Z^6_{g''}O_{x'''}$,
$E = Z^7_{12}Cu_{h''}H_{i''}O_{y'''}$,
$Z^1 = $ W, Nb, Ta, Cr and/or Ce,
$Z^2 = $ Cu, Ni, Co, Fe, Mn and/or Zn,
$Z^3 = $ Sb and/or Bi,
$Z^4 = $ Li, Na, K, Rb, Cs and/or H,
$Z^5 = $ Mg, Ca, Sr and/or Ba,
$Z^6 = $ Si, Al, Ti and/or Zr,
$Z^7 = $ Mo, W, V, Nb and/or Ta, preferably Mo and/or W,
$a'' = $ from 1 to 8,
$b'' = $ from 0.2 to 5,
$c'' = $ from 0 to 23,
$d'' = $ from 0 to 50,
$e'' = $ from 0 to 2,
$f'' = $ from 0 to 5,
$g'' = $ from 0 to 50,
$h'' = $ from 4 to 30,
$i'' = $ from 0 to 20 and
$x'', y'' = $ numbers which are determined by the valency and frequency of the elements in IX other than oxygen and
$p, q = $ numbers other than zero whose p/q ratio is from 160:1 to 1:1, and which are obtainable by separately preforming a multimetal oxide composition E $$Z^7_{12}Cu_{h''}H_{i''}O_{y''} \quad \text{(E)}$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D $$MO_{12}V_{a''}Z^1_{b''}Z^2_{c''}Z^3_{d''}Z^4_{e''}Z^5_{f''}Z^6_{g''} \quad \text{(D)}$$

(starting composition 2) in the desired p:q ratio, drying the aqueous mixture which may result, and calcining the resulting dry precursor composition before or after drying at temperatures of from 250 to 600° C. to give the desired catalyst geometry.

Particularly relevant multimetal oxide compositions IX are those in which the preformed solid starting composition 1 is incorporated into an aqueous starting composition 2 at a temperature of <70° C. A detailed description of the preparation of multimetal oxide composition VI catalysts is contained, for example, in EP-A 668 104, DE-A 197 36 105, DE-A 100 46 928, DE-A 197 40 493 and DE-A 195 28 646.

With regard to the shaping, the statements made for the multimetal oxide composition VII catalysts apply to multimetal oxide composition IX catalysts.

Multimetal oxide catalysts which are particularly relevant in accordance with the invention for the "acrolein→acrylic acid" step are also those of DE-A 198 15 281, especially having multimetal oxide active compositions of the general formula I of this document.

With relevance in accordance with the invention, unsupported catalyst rings are used for the step from propylene to acrolein and coated catalyst rings for the step from acrolein to acrylic acid.

According to the invention, the temperature in the first reaction stage is appropriately from 270 to 450° C. or from 280 to 420° C., preferably from 300 to 380° C. According to the invention, the reaction temperature in the second reaction stage is appropriately from 200 to 370 or to 320° C., preferably from 220 to 300° C.

The process according to the invention is also of particular relevance when the active compositions for the catalysts of the first reaction stage comprise those whose specific surface area is from 0.1 to 120 m²/g, or from 0.2 to 50 m²/g, or from 1 to 20 m²/g, or from 2 to 10 m²/g The process according to the invention is also of particular relevance when the active compositions for the catalysts of the first reaction stage comprise those whose numerically most frequent pore diameter is from 0.1 to 1 μm.

It is also of particular relevance when the aforementioned numerically most frequently pore diameters and one of the aforementioned specific surface areas are present in combination in the active compositions for the catalysts of the first reaction stage.

Moreover, the process according to the invention is of particular significance when the proportion of different pore diameters in the total pore volume in the active compositions for the catalysts of the first reaction stage has the following distribution:

Pores having diameters in the range from <0.03 μm: ≧0 and ≦5% by volume.

Pores having diameters in the range from ≧0.003 μm to ≦0.1 μm: ≧3 and ≦20% by volume.

Pores having diameters in the range from >0.1 to <1 μm: ≧75 and ≦95% by volume and Pores having diameters in the range from ≧1 to ≦10 μm: ≧0 and ≦5% by volume.

The total pore volume for first-stage catalyst active compositions relevant in accordance with the invention is typically from 0.1 to 1.00 ml/g, usually from 0.10 to 0.80 ml/g, or from 0.20 to 0.40 ml/g.

Furthermore, the process according to the invention is of particular relevance when the active compositions for the catalysts of the second reaction stage comprise those whose specific surface area is from 0.1 to 150 m²/g, or from 0.2 to 50 m²/g, or from 1 to 20 m²/g, or from 2 to 10 m²/g. In addition, the process according to the invention is of particular relevance when the active compositions for the catalysts of the second reaction stage comprise those whose numerically most frequent pore diameter is from 0.1 to 1 μm.

It is also of particular relevance when the aforementioned numerically most frequent pore diameters and one of the aforementioned specific surface areas are present in combination in the active compositions for the catalysts of the second reaction stage.

The total pore volume for second-stage catalysts relevant in accordance with the invention is typically from 0.10 to 0.90 ml/g, or from 0.20 to 0.80 ml/g, or from 0.30 to 0.70 ml/g.

Moreover, the process according to the invention is of particular significance when the pore distribution in the active compositions for the catalysts of the second reaction stage is such that in each case at least 5% by volume, preferably at least 10% by volume, of the aforementioned total pore volume is accounted for by the diameter ranges from 0 to <1.0 μm, from 1.0 to <10 μm and from 10 μm to 100 μm.

The inventive procedure is also advantageous when the pore diameter distributions according to EP-A 293 859 are present in the second-stage catalyst active compositions. Every single statement made above on specific surface area, pore diameter, total pore volume and pore diameter distribution applies especially in relation to every single multimetal oxide composition mentioned as relevant in this document for catalysts of the first oxidation stage and of the second oxidation stage.

In principle, the volume-specific activity of the at least one first catalyst bed (especially fixed catalyst bed) within the first reaction stage in the process according to the invention may either be constant over the length of the flow path in flow direction of reaction gas mixture 1 or increase at least once (continuously or abruptly or in stages). At least one increase is preferred in accordance with the invention under the inventive criteria (minimum by-product formation). In all of the aforementioned cases, it is also advantageous when the active composition does not change over the length of the flow path within the first reaction stage.

The statements made above for the first reaction stage apply equally to the second reaction stage of the process according to the invention.

When the catalyst bed for the first reaction stage is a fixed catalyst bed, it is possible to prepare this fixed bed catalyst charge 1 in the process according to the invention by using only shaped catalyst bodies having multimetal oxide active composition or else substantially homogeneous mixtures of shaped catalyst bodies having multimetal oxide active composition and shaped bodies (shaped diluent bodies) which have no multimetal oxide active composition and behave substantially inertly with respect to the heterogeneously catalyzed gas phase oxidation. Useful materials for such inert shaped bodies are in principle all of those which are also suitable as support material for coated catalysts suitable in accordance with the invention. Useful such materials include, for example, porous or nonporous aluminum oxides, silicon dioxide, thorium dioxide, zirconium dioxide, silicon carbide, silicates such as magnesium silicate or aluminum silicate, or the steatite already mentioned.

The geometry of such inert shaped diluent bodies may in principle be as desired. In other words, they may be, for example, spheres, polygons, solid cylinders or else, like the shaped catalyst bodies having active composition, rings. Preferably in accordance with the invention, the inert shaped diluent bodies selected will be those whose geometry corresponds to that of the shaped catalyst bodies to be diluted with them (the above statements also apply to substantially homogeneous mixtures of shaped catalyst bodies having multimetal oxide active composition and shaped diluent bodies usable for the provision of a fixed bed catalyst charge 2 (fixed catalyst bed for the second reaction stage)).

It is advantageous when the chemical composition of the active composition used does not change over the fixed bed catalyst charge 1. In other words, the active composition used for an individual shaped catalyst body may be a mixture of different multimetal oxides, but the same mixture then has to be used for all shaped catalyst bodies of the fixed bed catalyst charge 1.

The volume-specific (i.e. normalized to the unit of volume) activity can be reduced in a simple manner by homogeneously diluting a basic amount of shaped catalyst bodies produced in a uniform manner with shaped diluent bodies. The higher the fraction of the shaped diluent bodies selected, the lower the amount of active composition, or catalyst activity, present in a certain volume of the bed.

A volume-specific activity increasing at least once in flow direction of the reaction gas mixture over fixed bed catalyst charge 1 can thus be attained for the process according to the invention in a simple manner, for example, by beginning the bed with a high fraction of inert shaped diluent bodies based on one type of shaped catalyst bodies, and then reducing this fraction of shaped diluent bodies in flow direction either continuously or, at least once or more than once, abruptly (for example in stages). When the content of shaped diluent bodies is left constant or no shaped diluent bodies at all are used additionally in fixed bed catalyst 1, the result is a constant volume-specific activity in flow direction of the reaction gas mixture over fixed bed catalyst charge 1. However, an increase in the volume-specific activity is also possible, for example, by, with constant geometry and active composition type of a shaped coated catalyst body, increasing the thickness of the active composition layer applied to the support, or, in a mixture of coated catalysts with the same geometry but with different proportion by weight of the active composition, increasing the proportion of shaped catalyst bodies with higher proportions by weight of active composition. A similar effect can also be achieved, for example, by, in mixtures of unsupported catalysts and of coated catalysts (with identical composition) altering the mixing ratio in an appropriate manner. It will be appreciated that the variants described can also be employed in combination.

Normally, the volume-specific activity will decrease once neither within fixed bed catalyst charge 1 nor within fixed bed catalyst charge 2 in flow direction of the reaction gas mixture.

Upstream and/or downstream of fixed bed catalyst charge 1 may be disposed beds consisting exclusively of inert material (for example only shaped diluent bodies) (for terminology purposes, they are not included in the fixed bed catalyst charge 1 in this document, since they do not comprise any shaped bodies which have multimetal oxide active composition). The shaped diluent bodies used for the inert bed may have the same geometry as the shaped catalyst bodies used in fixed bed catalyst charge 1. However, the geometry of the shaped diluent bodies used for the inert bed may also be different from the aforementioned geometry of the shaped catalyst bodies (for example, spherical instead of annular).

Preferably in accordance with the invention, fixed bed catalyst charge 1 in the process according to the invention is preferably structured in flow direction of the reaction gas mixture as follows.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), in each case of the total length of fixed bed catalyst 1, either only shaped catalyst bodies or one homogeneous mixture of shaped catalyst bodies and shaped diluent bodies (both preferably having substantially the same geometry), in which the proportion by weight of shaped diluent bodies (the mass densities of shaped catalyst bodies and of shaped diluent bodies generally differ only slightly) is normally from 5 to 40% by weight, or from 10 to 40% by weight, or from 20 to 40% by weight or from 25 to 35% by weight. Downstream of this first zone of fixed bed catalyst charge 1 is then disposed, advantageously in accordance with the invention, up to the end of the length of fixed bed catalyst charge 1 (i.e., for example, to a length of from 2.00 to 3.00 m, preferably from 2.50 to 3.00 m), either a bed of shaped catalyst bodies diluted only to a lesser extent (than in the first zone), or, most preferably, a sole (undiluted) bed of the same shaped catalyst bodies which have also been used in the first zone.

The aforementioned is especially true when the shaped catalyst bodies used in fixed bed catalyst charge 1 are unsupported catalyst rings or coated catalyst rings (especially those which are mentioned in this document as preferred). For the purposes of the aforementioned structuring, both the shaped catalyst bodies and the shaped diluent bodies in the process according to the invention advantageously have substantially the ring geometry 5 mm×3 mm×2 mm (external diameter× length×internal diameter).

In a manner corresponding to the way in which the volume-specific activity of fixed bed catalyst charge 1 can be varied, the volume-specific activity of fixed bed catalyst charge 2 can also be varied. In this case a corresponding inert bed may again be disposed upstream and/or downstream of the actual fixed bed catalyst charge 2.

Preferably in accordance with the invention, fixed bed catalyst charge 2 in the process according to the invention is structured as follows in flow direction of the reaction gas mixture.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), in each case of the total length of fixed bed catalyst 2, either only shaped catalyst bodies or a homogeneous mixture of shaped catalyst bodies and shaped diluent bodies (both preferably having substantially the same geometry), in which the proportion by weight of shaped diluent bodies (the mass densities of shaped catalyst bodies and of shaped diluent bodies generally differ only slightly) is normally from 10 to 50% by weight, preferably from 20 to 45% by weight and more preferably from 25 to 35% by weight. Downstream of this first zone is then disposed, advantageously in accordance with the invention, up to the end of the length of fixed bed catalyst charge 2 (i.e., for example, to a length of from 2.00 to 3.00 m, preferably from 2.50 to 3.00 m), either a bed of shaped catalyst bodies diluted only to a lesser extent (than in the first zone), or, most preferably, a sole bed of the same shaped catalyst bodies which have also been used in the first zone.

The aforementioned is especially true when the shaped catalyst bodies used in fixed bed catalyst charge 2 are coated catalyst rings (especially those which are mentioned in this document as preferred). For the purposes of the aforementioned structuring, both the shaped catalyst bodies or their support rings and the shaped diluent bodies in the process according to the invention advantageously have substantially the ring geometry 7 mm×3 mm×4 mm (external diameter× length×internal diameter).

Appropriately from an application point of view, the first reaction stage of the process according to the invention can be carried out, for example, in a tube bundle reactor charged with fixed bed catalyst charge 1 (and, if appropriate, inert beds upstream and/or downstream of it), as described, for example, in EP-B 700714.

In other words, in the simplest manner, the aforementioned charge in each case is disposed in the individual metal tubes of a tube bundle reactor and a heating medium (one-section method), generally a salt melt, is conducted around the metal tubes. Salt melt and reaction gas mixture may be conducted in simple cocurrent or countercurrent. However, the salt melt (the heating medium) may also be conducted around the tube bundle in a meandering manner viewed over the reactor, so that only viewed over the entire reactor does a occurrent or countercurrent to the flow direction of the reaction gas mixture exist. The flow rate of the heating medium (heat exchange medium) is typically such that the temperature rise (caused by the exothermicity of the reaction) of the heat exchange medium from the inlet point into the reactor to the outlet point from the reactor is from $\geq 0$ to 10° C., frequently from $\geq 2$ to 8° C., often from $\geq 3$ to 6° C. The inlet temperature of the heat exchange medium into the tube bundle reactor is generally from 300 to 360° C., frequently from 300 to 340° C.

Suitable heat exchange media are especially fluid heating media. It is particularly favorable to use melts of salts such as potassium nitrate, potassium nitrite, sodium nitrite and/or sodium nitrate, or of low-melting metals such as sodium, mercury and alloys of different metals.

Typically, the catalyst tubes in the aforementioned tube bundle reactors are manufactured from ferritic steel and typically have a wall thickness of from 1 to 3 mm. Their internal diameter is (in particular in the case of use of the catalyst ring geometries specified in this document) generally from 20 to 30 mm, frequently from 21 to 26 mm. Their length is typically from 2 to 4 m, frequently from 2.5 to 3.5 m. According to the invention, normally at least 60%, frequently at least 75%, of these are occupied by fixed bed catalyst charge 1. Appropriately from an application point of view, the number of catalyst tubes accommodated in the tube bundle vessel amounts to at least 5000, preferably to at least 10000. Frequently, the number of catalyst tubes accommodated in the reaction vessel is from 15000 to 30000 or to 40000. Tube bundle reactors having more than 50000 catalyst tubes are usually the exception. Within the vessel, the catalyst tubes are normally arranged in homogeneous distribution, the distribution appropriately being selected such that the separation of the central internal axes of immediately adjacent catalyst tubes (known as the catalyst tube pitch) is from 35 to 45 mm (cf., for example, EP-B 468290). A tube bundle reactor suitable for the process according to the invention is also disclosed by DE-A 10131126, DE-A 10137768, DE-A 10135498 and DE-A 10232967.

Appropriately, starting reaction gas mixture 1 is fed to fixed bed catalyst charge 1 preheated to the reaction temperature. This purpose can be served, for example, by a bed of inert material preceding a fixed bed catalyst charge.

It will be appreciated that the first reaction stage of the process according to the invention may also be carried out in a two-section (or multisection) tube bundle reactor, as described, for example, in DE-A 19910508, 19948523, 19910506 and 19948241. A preferred variant of a two-section tube bundle reactor which can be used in accordance with the invention is disclosed by DE-C 2830765. However, the two-section tube bundle reactors disclosed in DE-C 2513405, U.S. Pat. No. 3,147,084, DE-A 2201528, EP-A 383224 and DE-A 2903218 are also suitable for carrying out the first reaction stage of the process according to the invention.

In other words, in the simplest manner, the fixed bed catalyst charge 1 to be used in accordance with the invention (possibly with downstream and/or upstream inert beds) is disposed in the metal tubes of a tube bundle reactor and two substantially spatially separated heating media, generally salt melts, are conducted around the metal tubes. The tube section over which the particular salt bath extends represents a reaction section in accordance with the invention. In other words, in the simplest manner, for example, a salt bath A flows around that section of the tubes (reaction section A) in which the oxidative conversion of propene (in single pass) proceeds until a conversion in the range from 40 to 80 mol % is achieved, and a salt bath B flows around the section of the tubes (reaction section B) in which the subsequent oxidative conversion of propene (in single pass) proceeds until a conversion value of at least 90 mol % is achieved (if required, the reaction sections A, B to be used in accordance with the invention may be followed by further reaction sections which are maintained at individual temperatures).

It is appropriate from an application point of view for the first reaction stage of the process according to the invention not to comprise any further reaction sections. In other words, salt bath B appropriately flows around the section of the tubes in which the subsequent oxidative conversion of propene (in single pass) proceeds up a conversion value of $\geq$90 mol %, or $\geq$92 mol %, or $\geq$94 mol %, or $\geq$96 mol % or more.

Typically, the beginning of reaction section B lies beyond the hotspot maximum of reaction section A. The hotspot maximum of reaction section B is normally below the hotspot maximum temperature of reaction section A.

According to the invention, both salt baths A, B can be conducted in cocurrent or in countercurrent through the space surrounding the reaction tubes relative to the flow direction of the reaction gas mixture flowing through the reaction tubes. It is of course also possible in accordance with the invention to employ cocurrent flow in reaction section A and countercurrent flow in reaction section B (or vice versa).

In all of the aforementioned cases, it is of course possible to superimpose a transverse flow on the parallel flow of the salt melt, relative to the reaction tubes, taking place within the particular reaction section, so that the individual reaction section corresponds to a tube bundle reactor as described in EP-A 700 714 or in EP-A 700 893, which results overall in a meandering flow profile of the heat exchange medium in a longitudinal section through the catalyst tube bundle.

In the two-section method too, starting reaction gas mixture 1 is appropriately fed preheated to the reaction temperature to fixed bed catalyst charge 1.

In the two-section tube bundle reactors too, the catalyst tubes are typically manufactured from ferritic steel and typically have a wall thickness of from 1 to 3 mm. Their internal diameter is generally from 20 to 30 mm, frequently from 21 to 26 mm. Their length is appropriately from 2 to 4 m, preferably from 2.5 to 3.5 m. In each temperature section, the fixed bed catalyst charge 1 occupies at least 60%, or at least 75%, or at least 90%, of the length of the section. Any remaining length is optionally occupied by an inert bed. It is advantageous from an application point of view for the number of catalyst tubes accommodated in the tube bundle vessel to be at least 5000, preferably at least 10 000. Frequently, the number of catalyst tubes accommodated in the reaction vessel is from 15 000 to 30 000 or to 40 000. Tube bundle reactors having a number of catalyst tubes above 50 000 are usually exceptional. Within the vessel, the catalyst tubes are normally distributed homogeneously, and the distribution is appropriately selected in such a way that the separation of the central internal axes of immediately adjacent catalyst tubes (known as the catalyst tube pitch) is from 35 to 45 mm (cf., for example, EP-B 468 290).

Suitable heat exchange media for the two-zone method are also in particular fluid heating media. It is particularly favorable to use melts of salts such as potassium nitrate, potassium nitrite, sodium nitrite and/or sodium nitrate, or of low-melting metals such as sodium, mercury and also alloys of different metals.

In general, in all of the aforementioned flow arrangements in the two-section tube bundle reactors, the flow rate within the two heat exchange medium circuits required is selected in such a way that the temperature of the heat exchange medium rises from the entrance into the reaction section to the exit from the reaction section (as a result of the exothermicity of the reaction) by from 0 to 15° C. In other words, the aforementioned $\Delta T$ may, in accordance with the invention, be from 1 to 10° C., or from 2 to 8° C., or from 3 to 60° C.

According to the invention, the entrance temperature of the heat exchange medium into reaction section A is normally from 300 to 340° C. According to the invention, the entrance temperature of the heat exchange medium into reaction section B is normally firstly from 305 to 380° C., and is secondly simultaneously at least $\geq$0° C., or at least 5° C., above the entrance temperature of the heat exchange medium entering reaction section A. If appropriate, this temperature difference may be $\leq$0° C.

At high propene loadings, the entrance temperature of the heat exchange medium into reaction section B is appropriately at least 10° C. above the entrance temperature of the heat exchange medium entering reaction section A. The difference between the entrance temperatures into reaction section A and B may, in accordance with the invention, thus be up to 20° C., up to 25° C., up to 30° C., up to 40° C., up to 45° C. or up to 50° C. Normally, the aforementioned temperature difference will, though, not be more than 50° C. The higher the propylene loading on fixed bed catalyst charge 1 is selected in the process according to the invention, the greater should be the difference between the entrance temperature of the heat exchange medium into reaction section A and the entrance temperature of the heat exchange medium into reaction section B.

Advantageously, the entrance temperature of the heat exchange medium into reaction section B is, in accordance with the invention, from 330 to 370° C. and particularly advantageously from 340 to 370° C.

It will be appreciated that the two reaction sections A, B in the process according to the invention may also be realized in spatially separate tube bundle reactors. If required, a heat exchanger can also be mounted between the two reaction sections A, B.

It should also be pointed out once again here that, for an implementation of reaction stage 1 of the process according to the invention, it is possible in particular also to use the two-section tube bundle reactor type described in DE-B 2201528, which includes the possibility of removing a portion of the hotter heat exchange medium of reaction section B to reaction section A, in order if appropriate to heat a cold starting reaction gas mixture or a cold cycle gas. The tube bundle characteristics within an individual reaction section may also be configured as described in EP-A 382098.

According to the invention, it has been found to be appropriate to cool the product gas mixture leaving the first reaction stage before entry into the second reaction stage, in order thus to suppress subsequent complete combustion of parts of the acrolein formed in the first reaction stage. For this purpose, an aftercooler is typically connected between the two reaction stages. In the simplest case, this may be an indirect tube bundle heat transferrer. In this case, the product gas mixture is generally conducted through the tubes and a heat exchange medium is conducted around the tubes, whose type may correspond to the heat exchange media recommended for the tube bundle reactors. Advantageously, the tube interior is filled with inert random packings (for example spirals of stainless steel, rings of steatite, spheres of steatite, etc). These improve the heat exchange and capture any molybdenum trioxide subliming out of the fixed bed catalyst charge of the first reaction stage before it enters the second reaction stage. It is advantageous for the aftercooler to be manufactured from stainless steel coated with zinc silicate primer.

In general, the propene conversion based on single pass in the process according to the invention in the first reaction stage will be $\geq 92$ mol % or $\geq 94$ mol %, or $>96$ mol %, or more. According to the invention, the resulting selectivity $S^{AA}$ of acrolein formation and of acrylic acid by-product formation together in single pass in the first reaction stage will regularly be $\geq 85$ mol % or $\geq 90$ mol %, in many cases $\geq 92$ mol % or $\geq 94$ mol %, frequently $\geq 95$ mol % or $\geq 96$ mol % or $\geq 97$ mol %.

The process according to the invention is suitable for propene loadings of the fixed bed catalyst charge 1 of $\geq 80$ l(STP)/l·h, or of $\geq 100$ l(STP)/l·h, or of $\geq 120$ l(STP)/l·h, or of $\geq 140$ l(STP)/l·h, or of $\geq 165$ l(STP)/l·h, or of $\geq 170$ l(STP)/l·h or $\geq 175$ l(STP)/l·h or $\geq 180$ l(STP)/l·h, but also for propene loadings of fixed bed catalyst charge 1 of $\geq 185$ l(STP)/l·h, or $\geq 190$ l(STP)/l·h or $\geq 200$ l(STP)/l·h or $\geq 210$ l(STP)/l·h, and also for loading values of $\geq 220$ l(STP)/l·h or $\geq 230$ l(STP)/l·h or $\geq 240$ l(STP)/l·h or $\geq 250$ l(STP)/l·h.

With increasing propene loading, the two-section method described is preferred over the one-section method described in the first reaction stage.

Normally, the propene loading of the first fixed bed catalyst charge in the process according to the invention will not exceed 600 l(STP)/l·h. Typically, the propene loadings of the fixed bed catalyst charge 1 in the process according to the invention are at values of $\leq 300$ l(STP)/l·h, frequently at values of $\leq 250$ l(STP)/l·h.

The working pressure in the process according to the invention in the first reaction stage may be either be below standard pressure (for example up to 0.5 bar; the reaction mixture is sucked through) or above standard pressure. Typically, the working pressure in the first reaction stage is at values of from 1 to 5 bar, frequently from 1.5 to 3.5 bar. Normally, the reaction pressure in the first reaction stage will not exceed 100 bar.

Useful sources for the molecular oxygen required in the first reaction stage are both air and air depleted in molecular nitrogen.

It is appropriate from an application point of view to cool the product gas mixture of the first reaction stage to a temperature of from 210 to 290° C., frequently from 230 to 280° C. or from 250 to 270° C. in the aftercooler already mentioned. The product gas mixture of the first reaction stage can quite possibly be cooled to temperatures which are below the temperature of the second reaction stage. However, the aftercooling described is in no way obligatory and can generally be dispensed with especially when the path of the product gas mixture from the first reaction stage into the second reaction stage is kept short. Typically, the process according to the invention is also realized in such a way that the oxygen requirement in the second reaction stage is not already covered by an appropriately high oxygen content of starting reaction gas mixture 1, but rather that the oxygen required is added in the region between the first and second reaction stage. This can be done before, during, after and/or for aftercooling. Useful sources for the molecular oxygen required in the second reaction stage are both pure oxygen and mixtures of oxygen and inert gas, for example air or air depleted in molecular nitrogen (for example $\geq 90$% by volume of $O_2$, $\leq 10$% by volume of $N_2$). The oxygen source is regularly added compressed to the reaction pressure. It will be appreciated that the oxygen requirement in the second reaction stage in the process according to the invention may already be covered by an appropriately high oxygen requirement in the first reaction stage.

The working pressure in the process according to the invention in the second reaction stage, as in reaction stage 1, may be either below standard pressure (for example up to 0.5 bar) or above standard pressure. According to the invention, the working pressure in the second reaction stage will typically be at values of from 1 to 5 bar, frequently from 1 to 3 bar. Normally, the reaction pressure in the second reaction stage will not exceed 100 bar.

Just like the first reaction stage, the second reaction stage of the process according to the invention can be carried out in a simple manner in a tube bundle reactor charged with fixed bed catalyst 2, as described, for example, in EP-A 700893. The inert beds preceding and/or following fixed bed catalyst charge 2 can complete the charge.

In other words, in the simplest manner, the fixed bed 2 to be used in catalyst 2 accordance with the invention and any inert beds used additionally are disposed in the metal tubes of a tube bundle reactor and a heating medium (one-section method), generally a salt melt, is conducted around the metal tubes. Salt melt and reaction gas mixture may be conducted in simple occurrent or countercurrent. However, the heating medium may also be conducted around the tube bundle in a meandering manner viewed over the reactor, so that only viewed over the entire reactor does a occurrent or countercurrent to the flow direction of the reaction gas mixture exist. The volume flow rate of the heating medium (heat exchange medium) is typically such that the temperature rise (caused by the exothermicity of the reaction) of the heat exchange medium from the entrance point into the reactor to the exit point from the reactor is from $\geq 0$ to $10°$ C., frequently from $\geq 2$ to $8°$ C., often from $\geq 3$ to $6°$ C. The entrance temperature of the heat exchange medium into the tube bundle reactor is generally from 230 to $300°$ C., frequently from 245 to $285°$ C., or from 255 to $275°$ C. Suitable heat exchange media are the same fluid heating media as have already been described for the first reaction stage.

Appropriately, starting reaction gas mixture 2 is fed to fixed bed catalyst charge 2 preheated to the reaction temperature. For the dimensioning of the catalyst tubes, the catalyst tube material, the catalyst tube number and their charge with fixed bed catalyst charge 2/inert bed, the same applies as was stated for the tube bundle reactor of the first reaction stage.

In general, a one-section method of the first reaction stage is combined with a one-section method of the second reaction stage, the relative flow of reaction gas mixture and heating medium in both stages being selected identically.

However, it will be appreciated that the second reaction stage of the process according to the invention may also, in a manner corresponding to the first reaction stage, be realized as two spatially successive reaction sections C, D, in which case the temperature of reaction section C (this always means the temperature of the entering salt bath or heat carrier in general) is appropriately from 230 to $270°$ C. and the temperature of reaction section D is from 250 to $300°$ C. and simultaneously at least $\geq 0°$ C., or at least $\geq 5°$ C., above the temperature of reaction zone C. If appropriate, this temperature difference may also be $\leq 0°$ C.

Reaction section C extends preferably up to an acrolein conversion of from 65 to 80 mol %. Moreover, the temperature of reaction section C is advantageously from 245 to $260°$ C. The temperature of reaction section D at high acrolein loadings is preferably from 5 to $10°$ C. above the temperature of reaction section C and is advantageously from 260 to $285°$ C. For the two-section method of the second reaction stage 2, with regard to the reactor, for the dimensioning of the catalyst tubes, the catalyst tube material, the catalyst tube number and their charge with fixed bed catalyst 2/inert bed, the statements made for the two-section tube bundle reactor of the first reaction stage apply.

The higher the acrolein loading of fixed bed catalyst charge 2 is selected in the process according to the invention, the greater the preference for the two-section method over the one-section method and the greater the difference between the temperature of reaction section C and the temperature of reaction section D should be selected. Normally, the aforementioned temperature difference will, though, not be more than $40°$ C. In other words, the difference between the temperature of reaction section C and the temperature of reaction section D may, in accordance with the invention, be up to $15°$ C., up to $25°$ C., up to $30°$ C., up to $35°$ C. or up to $40°$ C.

Generally, in the process according to the invention, the acrolein conversion based on single pass of the second reaction stage may be $\geq 90$ mol %, or $\geq 92$ mol %, or $\geq 94$ mol %, or $\geq 96$ mol %, or $\geq 98$ mol % and frequently even $\geq 99$ mol %. The selectivity of acrylic acid formation, based on the acrolein converted, may regularly be $\geq 92$ mol %, or $\geq 94$ mol %, frequently $\geq 95$ mol % or $\geq 96$ mol % or $\geq 97$ mol %.

The process according to the invention is suitable for acrolein loadings of fixed bed catalyst charge 2 of $\geq 80$ l(STP)/l·h, or of $\geq 100$ l(STP)/l·h, or of $\geq 120$ l(STP)/l·h, or of $\geq 140$ l(STP)/l·h or $\geq 150$ l(STP)/l·h, or of $\geq 160$ l(STP)/l·h or $\geq 170$ l(STP)/l·h, or $\geq 175$ l(STP)/l·h or $\geq 180$ l(STP)/l·h, but also at acrolein loadings of fixed bed catalyst charge 2 of $\geq 185$ l(STP)/l·h, or of $\geq 190$ l(STP)/l·h or $\geq 200$ l(STP)/l·h, or $\geq 210$ l(STP)/l·h, and also at loading values of $\geq 220$ l(STP)/l·h, or $\geq 230$ l(STP)l·h or 240 l(STP)/l·h, or $\geq 250$ l(STP)/l·h.

Preferably in accordance with the invention, no secondary gas consisting only of inert gas is metered in between the first and second reaction stage.

Normally, the acrolein loading of the second fixed bed catalyst charge in the process according to the invention will not exceed the value of 600 l(STP)/l·h. Typically, the acrolein loadings of fixed bed catalyst charge 2 in the process according to the invention are, without significant loss of conversion and selectivity, at values of $\geq 300$ l(STP)/l·h, frequently at values of $\leq 250$ l(STP)/l·h.

In general, the acrolein loading of fixed bed catalyst charge 2 in the process according to the invention will be about 10 l(STP)/l·h, frequently about 20 or 25 l(STP)/l·h, below the propene loading of fixed bed catalyst charge 1. This is primarily attributable to the fact that both conversion and selectivity for acrolein in the first reaction stage generally do not attain 100%. Moreover, the oxygen demand of the second reaction stage is typically covered by air as a secondary gas. With increasing acrolein loading, the two-section method described is preferred over the one-section method performed in the second reaction stage.

Remarkably, the selectivity of acrylic acid formation assessed over both reaction stages in the process according to the invention, based on propene converted, even at the highest propene and acrolein loadings, may generally be at values of $\geq 83$ mol %, frequently at $\geq 85$ mol % or $\geq 88$ mol %, often at $\geq 90$ mol % or $\geq 93$ mol % or more.

In an appropriate manner from an application point of view, the second reaction stage of the process according to the invention is carried out in a two-section tube bundle reactor. A preferred variant of a two-section tube bundle reactor usable in accordance with the invention for the second reaction stage is disclosed by DE C 2830765. However, the two-section tube bundle reactors disclosed in DE-C 2513405, U.S. Pat. No. 3,147,084, DE-A 2201528, EP-A 383224 and DE-A 2903582 are also suitable for a performance of the second reaction stage of the process according to the invention.

In other words, in a simple manner, the fixed bed catalyst charge 2 (including any inert beds) to be used in accordance with the invention is disposed in the metal tubes of a tube bundle reactor and two substantially spatially separated heating media, generally salt melts, are conducted around the metal tubes. According to the invention, the tube section over which the respective salt bath extends represents a reaction section.

In other words, in a simple manner, for example, a salt bath C flows around those sections of the tubes (reaction section C) in which the oxidative conversion of acrolein (in single pass) proceeds until a conversion value in the range from 55 to 85 mol % is achieved, and a salt bath D flows around the section of the tubes (reaction section D) in which the subsequent oxidative conversion of acrolein (in single pass) proceeds until a conversion value of at least 90 mol % is achieved (if required, the reaction zones C, D to be used in accordance with the invention may be followed by further reaction zones which are maintained at individual temperatures).

It is appropriate from an application point of view for reaction stage 2 of the process according to the invention not to comprise any further reaction sections. In other words, salt bath D appropriately flows around the section of the tubes in which the subsequent oxidative conversion of acrolein (in single pass) proceeds up to a conversion value of ≧92 mol %, or ≧94 mol % or ≧96 mol % or ≧98 mol % and frequently even ≧99 mol % or more.

Typically, the beginning of temperature zone D lies beyond the hotspot maximum of temperature zone C. The temperature of the hotspot maximum of reaction section D is normally below the hotspot maximum temperature of reaction section C.

According to the invention, both salt baths C, D can be conducted in occurrent or in countercurrent through the space surrounding the reaction tubes relative to the flow direction of the reaction gas mixture flowing through the reaction tubes. It is of course also possible in accordance with the invention to employ occurrent flow in reaction section C and countercurrent flow in reaction section D (or vice versa).

In all of the aforementioned cases, it is of course possible to superimpose a transverse flow on the parallel flow of the salt melt, relative to the reaction tubes, taking place within the particular reaction section, so that the individual reaction section corresponds to a tube bundle reactor as described in EP-A 700 714 or in EP-A 700 893, which results overall in a meandering flow profile of the heat exchange medium in a longitudinal section through the catalyst tube bundle.

Typically, the catalyst tubes in the aforementioned two-zone tube bundle reactors (just like in the tube bundle reactors of the one-zone method) are manufactured from ferritic steel and typically have a wall thickness of from 1 to 3 mm. Their internal diameter is generally from 20 to 30 mm, frequently from 22 to 26 mm. Their length is advantageously from 3 to 4 m, preferably 3.5 m. In each temperature zone, fixed bed catalyst charge 2 occupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5000, preferably at least 10 000. Frequently, the number of catalyst tubes accommodated in the reaction vessel is from 15 000 to 30 000 or 40 000. Tube bundle reactors having a number of catalyst tubes above 50 000 are usually exceptional. Within the vessel, the catalyst tubes are normally homogeneously distributed, and the distribution is advantageously selected in such a way that the separation of the central internal axes of immediately adjacent catalyst tubes (known as the catalyst tube pitch) is from 35 to 45 mm (cf. EP-B 468 290).

Suitable heat exchange media are in particular fluid heating media. It is particularly favorable to use melts of salts such as potassium nitrate, potassium nitrite, sodium nitrite and/or sodium nitrate, or of low-melting metals such as sodium, mercury and also alloys of different metals.

In general, in all of the abovementioned flow arrangements in the two-section tube bundle reactors, the flow rate within the two heat exchange medium circuits required is selected in such a way that the temperature of the heat exchange medium rises from the entrance into the reaction zone to the exit from the reaction zone by from 0 to 15° C. In other words, the aforementioned ΔT may, in accordance with the invention, be from 1 to 10° C., or from 2 to 8° C., or from 3 to 60° C.

The entrance temperature of the heat exchange medium into reaction section C in an inventive two-section method in the second reaction stage is normally from 230 to 270° C. The entrance temperature of the heat exchange medium into reaction section D is, in accordance with the invention, normally firstly from 250 to 300° C. and is secondly simultaneously at least ≧0° C., or at least ≧5° C., above the entrance temperature of the heat exchange medium entering reaction section C.

At high acrolein loadings, the entrance temperature of the heat exchange medium into reaction section D is preferably from 5 to 10° C. above the entrance temperature of the heat exchange medium entering reaction section C. According to the invention, the difference between the entrance temperatures into reaction sections C and D may also be up to 15° C., up to 25° C., up to 30° C., up to 35° C. or up to 40° C. Normally, the aforementioned temperature will, though, not be more than 50° C. The higher the acrolein loading of catalyst bed 2 is selected in the process according to the invention, the greater should be the difference between the entrance temperature of the heat exchange medium into reaction section C and the entrance temperature of the heat exchange medium into reaction section D. The entrance temperature of the heat exchange medium into reaction section C is preferably from 245 to 260° C. and the entrance temperature into reaction section D from 260 to 285° C.

It will be appreciated that the two reaction sections C, D in the process according to the invention may also be realized in separate tube bundle reactors. If required, a heat exchanger may also be mounted between the two reaction sections C, D.

It should also be pointed out once again here that, for a performance of the second reaction stage of the process according to the invention, it is possible in particular to use the two-section tube bundle reactor type which is described in DE-B 2201528 and includes the possibility of removing a portion of the hotter heat exchange medium of reaction section D to reaction section C, in order if appropriate to heat a starting reaction gas mixture 2 which is too cold or a cold cycle gas. Moreover, the tube bundle characteristics within an individual reaction section may be configured as described in EP-A 382 098.

It is of course also possible in the process according to the invention to combine two one-section tube bundle reactors for the two reaction stages to give a single two-section reactor to be operated in another manner, as described, for example, in DE-C 2830765, in EP-A 911313 and in EP-A 383 224. In this case, the first reaction stage is implemented in the first reaction section and the second reaction stage in the second reaction section of the two-zone tube bundle reactor.

In an entirely corresponding manner, it is also possible to combine one one-section tube bundle reactor and one two-section tube bundle reactor or two two-section tube bundle reactors to a single tube bundle reactor in each case, which then has three or four temperature sections and is described, for example, in WO 01/36364.

In this case, for example, the first reaction stage can be carried out in the first reaction section and the second reaction stage in the two downstream reaction sections of the three-section tube bundle reactor. Alternatively, for example, the first reaction stage may be carried out in the first two reaction sections and the second reaction stage in the two downstream reaction sections of the four-section tube bundle reactor, and so forth. The salt bath temperature of the individual temperature sections may be configured as described in the case of the spatially separate tube bundle reactors. Normally, an inert bed is disposed in these cases between fixed bed catalyst charge 1 and fixed bed catalyst charge 2. However, it is also possible to dispense with such an intermediate inert bed. The length of the reaction tubes in the cases of combination in many cases corresponds to the sum of the lengths of the uncombined tube bundle reactors. The process according to the invention can of course also be performed analogously to the procedures described in the documents EP-A 990636 and EP-A 1106598.

In general, starting reaction gas mixture 1 in the process according to the invention comprises from 3 to 25% by volume, in many cases from 5 to 20% by volume and usually from 6 to 13% by volume of propylene.

According to the invention, the content of molecular oxygen in starting reaction gas mixture 1 should be such that the molar ratio $V_1$ of $O_2$ present in starting reaction gas mixture 1 to $C_3H_6$ present in the starting reaction gas mixture is $\geq 1$. Typically, $V_1$ in the process according to the invention is $\geq 1$ and $\leq 3$, usually $\geq 1.3$ and $\leq 2.5$, often from $\geq 1.5$ to $\leq 2.3$. The amount of molecular oxygen in starting reaction gas mixture 2 is normally such that the molar ratio of $O_2$ present in starting reaction gas mixture 2 to acrolein present in starting reaction gas mixture 2 is from $\geq 0.5$ to $\leq 2$, frequently from $\geq 0.75$ to $\leq 1.5$. It is favorable when product gas mixture 2 also comprises up to 5% by volume or up to 3% by volume of molecular oxygen.

The inventive procedure is particularly relevant when starting reaction gas mixture 1 comprises steam, since it promotes the conversion of the cyclopropane.

Starting reaction gas mixture 1 may also comprise up to 25% by volume (for example from 0.01 or 0.1, or 0.5, or 2 to 25% by volume) of $CO_2$.

Especially when the source used for the molecular oxygen in the process according to the invention is air, starting reaction gas mixture 1 will comprise molecular nitrogen as an inert diluent gas. In principle, starting reaction gas mixture 1 in the process according to the invention may comprise $\geq 1\%$ by volume, or $\geq 5\%$ by volume, or $\geq 10\%$ by volume, or $\geq 20\%$ by volume, or $\geq 30\%$ by volume, or $\geq 40\%$ by volume of molecular nitrogen. In general, the content in starting reaction gas mixture 1 of molecular nitrogen will, however, be at values of $\leq 80$ mol %, or $\leq 70$ mol %, or $\leq 60$ mol %.

The process according to the invention therefore comprises especially those embodiments in which starting reaction gas mixture 1 comprises from >0 to 35% by volume, frequently from 1 to 25% by volume, or from 5 to 15% by volume, or to 10% by volume of $H_2O$.

Typical starting reaction gas mixtures 1 are, for example, those which comprise:

| | |
|---|---|
| from 6 to 11% by volume of | propene, |
| from 6 to 12% by volume of | water, |
| from $\geq 0$ to 5% by volume of | of constituents other than propene, water, oxygen, cyclopropane and nitrogen, |
| | sufficient molecular oxygen that $V_1$ is from 1 to 3, |
| | from >0 up to 3 mol %, based on propene present, of cyclopropane, and, as the remainder up to 100% by volume of the total amount, molecular nitrogen. |

According to the invention, starting reaction gas mixture 1 may also comprise up to 70% by volume, or up to 60% by volume, or up to 50% by volume, or up to 40% by volume, or up to 30% by volume, or up to 20% by volume, or up to 10% by volume of propane. Frequently, this propane content is $\geq 0.01$, or $\geq 0.03$, or $\geq 0.05$, or $\geq 0.1$, or $\geq 1\%$ by volume. In general, starting reaction gas mixture 1 comprises $\leq 10\%$ by volume, in many cases $\leq 5\%$ by volume of propane. In the process according to the invention, this propane may be added deliberately as an inert diluent gas. When it is added in the form of crude propane comprising impurities, it may also comprise cyclopropane.

In other words, inventive starting reaction gas mixtures 1 may also comprise:

| | |
|---|---|
| from 6 to 9% by volume of | propylene, |
| from 8 to 18% by volume of | molecular oxygen, |
| from 6 to 30% by volume of | propane and |
| from 32 to 72% by volume of | molecular nitrogen. |

Inventive starting reaction gas mixtures 2 may comprise:

| | |
|---|---|
| from 4.5 to 8% by volume of | acrolein, |
| from 2.25 to 9% by volume of | molecular oxygen, |
| from 6 to 30% by volume of | propane, |
| from 32 to 72% by volume of | molecular nitrogen, |
| from 5 to 30% by volume of | steam. |

However, inventive starting reaction gas mixtures 2 may also comprise up to 20% by volume of $H_2$.

In other words, reaction gas mixtures 1 of the process according to the invention may also comprise:

| | |
|---|---|
| from 4 to 25% by volume of | propylene, |
| from 6 to 70% by volume of | propane, |
| from 5 to 60% by volume of | $H_2O$, |
| from 8 to 65% by volume of | $O_2$ and |
| from 0.3 to 20% by volume of | $H_2$. |

The process according to the invention is also favorable when starting reaction gas mixture 1 comprises from 0.1 to 30% by volume of $CO_2$.

Starting reaction gas mixtures 2 possible in accordance with the invention may also comprise:

| | |
|---|---|
| from 3 to 25% by volume of | acrolein |
| from 5 to 65% by volume of | molecular oxygen, |
| from 6 to 70% by volume of | propane, |
| from 0.3 to 20% by volume of | molecular hydrogen and |
| from 8 to 65% by volume of | steam. |

Finally, it should be emphasized that the present invention also comprises a process in which the acrylic acid removed crystallizatively in the second separation zone is melted and is followed by at least one process for free-radical polymerization, in which molten acrylic acid crystals are polymerized free-radically to prepare polymers. In this document, propane without further addition means n-propane.

The present invention further comprises processes in which the process according to the invention for preparing acrylic acid is followed by a process for preparing acrylic esters, in which acrylic acid prepared in accordance with the invention is esterified with alcohols (preferably alkanols, more preferably $C_1$- to $C_{12}$-alkanols), generally under acid catalysis. The process of esterification may in turn be followed by a process for free-radical polymerization, in which acrylic esters prepared in this way are polymerized.

It should also be emphasized once again that at least a portion of the residual gas remaining in the conversion (in separation zone 1) of the acrylic acid from product gas mixture 2 into the condensed phase can be recycled into the first reaction stage and/or into the second reaction stage.

It is also possible to feed the propylene present in starting reaction gas mixture 1 to starting reaction gas mixture 1 at least partly from a partial dehydrogenation (for example homogeneously and/or heterogeneously catalyzed, in the presence and/or with exclusion of molecular oxygen) (generally in the presence of unconverted propane). In the aforementioned case, at least a portion of the residual gas remaining in the conversion of the acrylic acid from product gas mixture 2 into the condensed phase can be recycled into the partial dehydrogenation of propane.

The cyclopropane content of starting reaction gas mixture 1 can (like all other contents of starting reaction gas mixture 1) be determined by gas chromatography without any problem. Analysis of condensed phase of starting reaction gas mixture 1 allows the detection limit for cyclopropane and other $C_3$ hydrocarbons to be extended.

Examples and Comparative Examples

I. Two-stage Heterogeneously Catalyzed Partial Oxidation of Propylene to Acrylic Acid in the Absence and in the Presence of Cyclopropane A) General experimental setup of the reaction apparatus
Reactor for the First Oxidation Stage (1st Reaction Stage)
The reactor consisted of a jacketed cylinder of stainless steel (cylindrical guide tube surrounded by a cylindrical outer vessel). The wall thicknesses were always from 2 to 5 mm.

The internal diameter of the outer cylinder was 91 mm. The internal diameter of the guide tube was approx. 60 mm.

At the top and bottom, the jacketed cylinder was concluded by a lid and base respectively.

The contact tube (total length 400 cm, internal diameter 26 mm, external diameter 30 mm, wall thickness 2 mm, stainless steel) was accommodated in the guide tube of the cylindrical vessel such that it just protruded in each case through the lid and base at the upper and lower end thereof (in a sealed manner). The heat exchange medium (salt melt consisting of 53% by weight of potassium nitrate, 40% by weight of sodium nitrite and 7% by weight of sodium nitrate) was enclosed in the cylindrical vessel. In order to ensure very uniform thermal boundary conditions at the outer wall of the contact tube over the entire length of contact tube within the cylindrical vessel (400 cm) the heat exchange medium was pumped in circulation by means of a propeller pump.

An electrical heater attached to the outer jacket regulated the temperature of the heat exchange medium to the desired level. Otherwise, there was air cooling.
Reactor charge:
Viewed over the first-stage reactor, the salt melt and the charge gas mixture of the first-stage reactor were conducted in cocurrent. The charge gas mixture entered the first-stage reactor at the bottom. It was conducted into the reaction tube with a temperature of 165° C. in each case.
The salt melt entered the cylindrical guide tube at the bottom with a temperature $T^{in}$ and left the cylindrical guide tube at the top with a temperature $T^{out}$ which was up to 2° C. above $T^{in}$.
$T^{in}$ was adjusted so as to always give rise to a propylene conversion of 97.8±0.1 mol % in single pass at the outlet of the first oxidation stage.
Catalyst tube charge:
(from the bottom upward) Section A: length 90 cm
Preliminary bed of steatite spheres of diameter of 4-5 mm.
Section B: length 100 cm
Catalyst charge of a homogeneous mixture of 30% by weight of steatite rings of geometry 5 mm×3 mm×2 mm (external diameter×length×internal diameter) and 70% by weight of unsupported catalyst from section C.

Section C: length 200 cm
Catalyst charge of annular (5 mm×3 mm×2 mm=external diameter×length×internal diameter) unsupported catalyst according to example 1 of DE-A 100 46 957 (stoichiometry: $[Bi_2W_2O_9.2WO_3]_{0.5}[Mo_{12}Co_{5.5}Fe_{2.94}Si_{1.59}K_{0.08}O_x]_1$).
Section D: length 10 cm
Downstream bed of steatite rings of geometry 7 mm×3 mm×4 mm (external diameter×length×internal diameter)
Intermediate Cooling and Intermediate Oxygen Feeding (Pure $O_2$ as Secondary Gas)

For the purpose of intermediate cooling (indirectly by means of air), the product gas mixture 1 leaving the first fixed bed reactor was conducted through a connecting tube (length 40 cm, internal diameter 26 mm, external diameter 30 mm, wall thickness 2 mm, stainless steel, wound around by 1 cm of insulating material) which was mounted centrally to a length of 20 cm, charged with an inert bed of steatite rings of geometry 7 mm×3 mm×4 mm (external diameter×length×internal diameter) and was flanged directly onto the first-stage catalyst tube.

The product gas mixture 1 always entered the connecting tube at a temperature of $>T^{in}$ (first stage) and left it with a temperature above 200° C. and below 270° C.

At the end of the connecting tube, molecular oxygen at the pressure level of product gas mixture 1 was metered into the cooled product gas mixture 1. The resulting gas mixture (charge gas mixture for the second oxidation stage) was conducted directly into the second-stage catalyst tube to which the abovementioned connecting tube was likewise flanged by its other end. The amount of molecular oxygen metered in was such that the molar ratio of $O_2$ present in the resulting gas mixture to acrolein present in the resulting gas mixture was 1.3.

Reactor for the Second Oxidation Stage (2nd Reaction Stage)

A catalyst tube fixed bed reactor was used which was of identical design to that for the first oxidation stage. Salt melt and charge gas mixture were conducted in occurrent viewed over the reactor. The salt melt entered at the bottom, the charge gas mixture likewise. The inlet temperature $T^{in}$ of the salt melt was adjusted so as always to result in an acrolein conversion of 99.3±0.1 mol % in single pass at the outlet of the second oxidation stage. $T^{out}$ of the salt melt was always up to 2° C. above $T^{in}$.
The Catalyst Tube Charge (From the Bottom Upward) was:
Section A:
Length 70 cm
Upstream bed of steatite rings of geometry 7 mm×3 mm×4 mm (external diameter×length×internal diameter).
Section B:
Length 100 cm
Catalyst charge of a homogeneous mixture of 30% by weight of steatite rings of geometry 7 mm×3 mm×4 mm (external diameter×length×internal diameter) and 70% by weight of coated catalyst from section C.
Section C:
Length 200 cm
Catalyst charge of annular (7 mm×3 mm×4 mm=external diameter×length×internal diameter) coated catalyst according to preparation
example 5 of DE-A 10046928 (stochiometry: $Mo_{12}V_3W_{1.2}Cu_{2.4}O_x$).
Section D:
Length 30 cm
Downstream bed of steatite spheres of diameter 4-5 mm.

B) Results achieved as a function of the composition of starting reaction gas mixture 1 of the first oxidation stage (the propene loading was set to 150 l(STP)/l·h; the selectivity of acrylic acid formation (assessed over both reaction stages based on propylene converted) was always ≧94 mol %).
a) The composition of starting reaction gas mixture 1 for the first oxidation stage comprised substantially (based on the total volume of starting reaction gas mixture 1):

| | |
|---|---|
| 6.3% by vol. of | propylene, |
| 28% by vol. of | propane, |
| X % by vol. of | cyclopropane, |
| 10.8% by vol. of | $O_2$, |
| 5% by vol. of | $H_2O$ and, |
| | as the remainder, $N_2$. |

From product gas mixture 2, the acrylic acid formed was condensed out by direct cooling with condensate which had been formed beforehand, cooled to 4° C. and polymerization-inhibited with hydroquinone. The table below shows the proportion by weight Y of the amount of propionic acid present in the condensate, based on the amount of acrylic acid present therein as a function of the amount X* of cyclopropane present in starting reaction gas mixture 1, but reported here in mol % relative to the molar amount of propylene present in the starting reaction gas mixture.

TABLE II

Crystallizative removal from an acrylic acid-containing liquid phase P

| X* (mol %) | Y (ppm by wt.) |
|---|---|
| 0.063 | 483 |
| 0.97 | 1114 |

II. Crystallizative Removal from an Acrylic Acid-Containing Liquid Phase P

The liquid phase P had the following contents:

| | |
|---|---|
| 95.201% by weight of | acrylic acid, |
| 0.042% by weight of | methacrylic acid, |
| 0.604% by weight of | benzaldehyde, |
| 0.062% by weight of | propionic acid, |
| 0.687% by weight of | furan-2-aldehyde, |
| 0.663% by weight of | acetic acid, |
| 0.004% by weight of | furan-3-aldehyde, |
| 0.002% by weight of | allyl acrylate |
| 0.009% by weight of | acrolein and |
| 2.20% by weight of | water. |

It was polymerization-inhibited by addition of 150 ppm by weight of monomethyl ether of hydroquinone (MEHQ) and <1000 ppm by weight of phenothiazine (based on acrylic acid present).

1800 g of the liquid phase P were charged into a stirred metal tank (capacity 2 l, helical stirrer with very close wall clearance).

At a cooling rate of 1 K/h, the temperature of the cooling liquid (water/glycol mixture) conducted in the jacket was lowered until the resulting crystal suspension (acrylic acid crystals suspended in residual melt) had a solids content of 18% by weight. A portion of the crystal suspension was then withdrawn and centrifuged on a laboratory centrifuge in a sieve cup equipped with a polypropylene filter fabric at 2000 revolutions per minute for 180 seconds, and the mother liquor thus remaining was spun off virtually fully. Analysis of the crystals remaining and of the mother liquor spun off gave rise to the depletion coefficients of 3.9 for propionic acid (the depletion coefficient is the quantitative ratio of propionic acid remaining in the mother liquor to propionic acid remaining in the crystals, in each case expressed as % by weight based on the total amount of mother liquor and the total amount of crystals respectively).

U.S. Provisional Patent Application No. 60/752,362, filed on Dec. 22, 2005, is incorporated into the present patent application by literature reference.

With regard to the above-mentioned teachings, numerous changes and deviations from the present invention are possible.

It can therefore be assumed that the invention, within the scope of the appended claims, can be performed differently from the way described specifically herein.

What is claimed is:

1. A process for heterogeneously catalyzed partial gas phase oxidation of propylene to acrylic acid, in which, in a first reaction zone, a starting reaction gas mixture 1 which comprises propylene, molecular oxygen and at least one inert diluent gas and comprises the molecular oxygen and the propylene in a molar $O_2$:$C_3H_6$ ratio of ≧1, in a first reaction stage at elevated temperature, is first conducted through at least one first catalyst bed whose catalysts have at least one multimetal oxide comprising Mo, Fe and Bi as the active composition, such that the propylene conversion in single pass through the catalyst bed is ≧90 mol % and the accompanying selectivity of acrolein formation and of acrylic acid by-product formation together is ≧80 mol %, the temperature of the product gas mixture 1 leaving the first reaction stage optionally is reduced by direct cooling or by indirect cooling or by direct and indirect cooling, and optionally a secondary gas in the form of molecular oxygen or inert gas or molecular oxygen and inert gas is added to product gas mixture 1, and then product gas mixture 1, as a starting reaction gas mixture 2 which comprises acrolein, molecular oxygen and at least one inert diluent gas and comprises the molecular oxygen and the acrolein in a molar $O_2$:$C_3H_4$ ratio of ≧0.5, in a second reaction stage at elevated temperature, is conducted through at least one second catalyst bed whose catalysts have at least one multimetal oxide comprising Mo and V as the active composition, such that the acrolein conversion in single pass through the catalyst bed is ≧90 mol % and the selectivity of acrylic acid formation assessed over both reaction stages, based on propylene converted, is ≧70 mol %, then the acrylic acid present in the product gas mixture 2 formed in the second reaction stage, in a first separation zone, is converted therefrom to the condensed phase and then, in a second separation zone, the acrylic acid is removed from the condensed phase by use of at least one thermal separation process,
wherein
starting reaction gas mixture 1, based on the molar amount of propylene present therein, comprises from 200 mol ppm up to 3 mol % of cyclopropane and the at least one thermal separation process in the second separation zone comprises at least one crystallizative removal of acrylic acid.

2. The process according to claim 1, wherein starting reaction gas mixture 1, based on the molar amount of propylene present therein, comprises from 200 mol ppm up to 2 mol % of cyclopropane.

3. The process according to claim 1, wherein starting reaction gas mixture 1, based on the molar amount of propylene present therein, comprises from 300 mol ppm to 1 mol % of cyclopropane.

4. The process according to claim 1, wherein the acrylic acid is converted from product gas mixture 2 into the condensed phase by absorptive measures.

5. The process according to claim 1, wherein the acrylic acid is converted from product gas mixture 2 into the condensed phase by condensative measures.

6. The process according to claim 1, wherein the acrylic acid is converted from product gas mixture 2 into the condensed phase by absorptive and condensative measures.

7. The process according to claim 4, wherein the absorbent used is water or an aqueous solution.

8. The process according to claim 1, wherein the acrylic acid is converted from product gas mixture 2 into the condensed phase by fractional condensation.

9. The process according to claim 1, wherein at least one crystallizative removal of the acrylic acid is effected in the second separation zone out of an acrylic acid-containing condensed phase obtained in the conversion of acrylic acid from product gas mixture 2 into the condensed phase carried out in the first separation zone.

10. The process according to claim 1, wherein at least one crystallizative removal of the acrylic acid is effected in the second separation zone out of a liquid phase which is the result of use of at least one thermal separation process other than a crystallization on the acrylic acid-containing condensed phase obtained in the first separation zone.

11. The process according to claim 1, wherein the at least one crystallizative removal of the acrylic acid is carried out as a fractional crystallization.

12. The process according to claim 1, wherein the at least one crystallizative removal of the acrylic acid is performed as a layer crystallization.

13. The process according to claim 1, wherein the at least one crystallizative removal of acrylic acid is a combination of dynamic and static layer crystallization.

14. The process according to claim 1, wherein the at least one crystallizative removal of the acrylic acid is performed as a suspension crystallization.

15. The process according to claim 14, wherein the separation of suspension crystals formed and mother liquor remaining is carried out in a wash column.

16. The process according to claim 1, wherein the at least one crystallizative removal of acrylic acid is effected out of a liquid phase which comprises water.

17. The process according to claim 1, wherein the acrylic acid removed by crystallization in the second separation zone is melted and at least one process for free-radical polymerization follows, in which molten acrylic acid crystals are free-radically polymerized to prepare polymers.

18. The process according to claim 1, wherein the at least one crystallizative removal of acrylic acid in the second separation zone is coupled with at least one indistinct separation process in the first and/or second separation zone by at least partly recycling the mother liquor remaining in the crystallizative acrylic acid removal into at least one of the indistinct separation processes.

19. The process according to claim 1, wherein the at least one multimetal oxide comprising Mo, Fe and Bi is one of formula IV

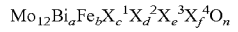 (IV)

where
X$^1$=nickel and/or cobalt,
X$^2$=thallium, an alkali metal and/or an alkaline earth metal,
X$^3$=zinc, phosphorus, arsenic, boron, antimony, tin, cerium, a lead and/or tungsten,
X$^4$=silicon, aluminum, titanium and/or zirconium,
a=from 0.5 to 5,
b=from 0.01 to 5,
c=from 0 to 10,
d=from 0 to 2,
e=from 0 to 8,
f=from 0 to 10 and
n=a number which is determined by the valency and frequency of the elements in IV other than oxygen.

20. The process according to claim 1, wherein the at least one multimetal oxide comprising Mo and V is one of formula VII

 (VII)

where
X$^1$=W, Nb, Ta, Cr and/or Ce,
X$^2$=Cu, Ni, Co, Fe, Mn and/or Zn,
X$^3$=Sb and/or Bi,
X$^4$=one or more alkali metals,
X$^5$=one or more alkaline earth metals,
X$^6$=Si, Al, Ti and/or Zr,
a=1 to 6,
b=0.2 to 4,
c=0.5 to 18,
d=0 to 40,
e=0 to 2,
f=0 to 4,
g=0 to 40 and
n=a number which is determined by the valency and frequency of the elements in VII other than oxygen.

21. The process according to claim 1, wherein a volume-specific activity of the at least one first catalyst bed increases at least once over a length of a flow path in flow direction of starting reaction gas mixture 1.

22. The process according to claim 1 wherein a volume-specific activity of the at least one second catalyst bed increases at least once over a length of the flow path in the flow direction of starting reaction gas mixture 2.

23. The process according to claim 1, wherein the at least one first catalyst bed is a fixed bed and a propene loading of the fixed bed is ≧120 l(STP)/l·h and ≦250 l(STP)/l·h.

24. The process according to claim 1, wherein starting reaction gas mixture 1 comprises from 6 to 13% by volume of propylene.

25. The process according to claim 1, wherein starting reaction gas mixture 1 comprises from >0 to 35% by volume of H$_2$O.

26. The process according to claim 1, wherein starting reaction gas mixture 1 comprises ≧0.01% by volume of propane.

27. The process according to claim 1, wherein at least a portion of the residual gas remaining in the conversion of acrylic acid from product gas mixture 2 into the condensed phase is recycled into the first reaction stage and/or into the second reaction stage.

28. The process according to claim 1, wherein the propylene present in starting reaction gas mixture 1 is supplied to starting reaction gas mixture 1 at least partly from a partial dehydrogenation of propane.

29. The process according to claim 28, wherein at least a portion of the residual gas remaining in the conversion of acrylic acid from product gas mixture 2 into the condensed phase is recycled into the partial dehydrogenation of propane.

30. The process of claim 1, further comprising:
reducing a temperature of the first product gas mixture leaving the first reaction stage by direct cooling or by indirect cooling or by direct and indirect cooling.

31. The process of claim 1, further comprising:
adding a secondary gas, in the form of (i) molecular oxygen, (ii) inert gas, or (iii) molecular oxygen and inert gas, to the first product gas mixture.

32. The process of claim 30, further comprising:
adding a secondary gas, in the form of (i) molecular oxygen, (ii) inert gas, or (iii) molecular oxygen and inert gas, to the first product gas mixture.

* * * * *